United States Patent
LaVon et al.

(10) Patent No.: US 9,724,251 B2
(45) Date of Patent: *Aug. 8, 2017

(54) REFASTENABLE ABSORBENT ARTICLE

(71) Applicant: The Procter & Gamble Company, Cincinnati, OH (US)

(72) Inventors: Gary Dean LaVon, Liberty Township, OH (US); Theodora Beck, Cincinnati, OH (US); Thomas Henrich, Cincinnati, OH (US); Aaron Joseph Meirose, Springfield Township, OH (US); Aaron Duane Seitz, Batavia Township, OH (US); Bret Darren Seitz, West Chester, OH (US); Bryan Keith Waye, Mason, OH (US); Kevin Michael Smith, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/080,974

(22) Filed: Mar. 25, 2016

(65) Prior Publication Data

US 2016/0250085 A1 Sep. 1, 2016

Related U.S. Application Data

(63) Continuation of application No. 13/010,040, filed on Jan. 20, 2011, now Pat. No. 9,427,362.

(Continued)

(51) Int. Cl.
*A61F 13/15* (2006.01)
*A61F 13/56* (2006.01)
(Continued)

(52) U.S. Cl.
CPC ........ *A61F 13/5622* (2013.01); *A61F 13/496* (2013.01); *A61F 13/4963* (2013.01);
(Continued)

(58) Field of Classification Search
CPC .... A61F 13/496; A61F 13/4963; A61F 13/58; A61F 13/581; A61F 13/60; A61F 13/62;
(Continued)

(56) References Cited

U.S. PATENT DOCUMENTS

RE26,151 E    1/1967   Duncan et al.
3,316,139 A   4/1967   Alford et al.
(Continued)

FOREIGN PATENT DOCUMENTS

EP   0 396 050 A2   11/1990
EP   0 396 512 A2   11/1990
(Continued)

OTHER PUBLICATIONS

PCT International Search Report, PCT/US2011/021828 date of mailing May 10, 2011.
(Continued)

*Primary Examiner* — Bradley Philips
(74) *Attorney, Agent, or Firm* — Richard L. Alexander

(57) ABSTRACT

An absorbent article is provided that comprises a front waist region, a back waist region, a crotch region disposed between the front waist region and the back waist region, a front waist end edge, a back waist end edge, a longitudinal axis extending from a mid-point of the front waist end edge to a mid-point of the back waist end edge, a first longitudinally extending side edge, a second longitudinally extending side edge, an exterior surface, an interior surface, a topsheet, a backsheet, and an absorbent core disposed between the backsheet and the topsheet. A portion of the front waist region and a portion of the back waist region are (Continued)

joined in a surface to surface relationship to form a pant comprising a first permanent side edge seam and a laterally opposed second permanent side edge seam. The first and second permanent side edge seams define an initial waist opening circumference and a pair of leg openings. The absorbent article comprises a first fastening component comprising a first fastening surface and a first attachment surface. The absorbent article comprises a second fastening component comprising a second fastening surface. The initial waist opening circumference formed by the first and second permanent side edge seams is configured to be opened. The first fastening surface and the second fastening surface are configured to be refastenably engaged and separated with each other.

17 Claims, 31 Drawing Sheets

Related U.S. Application Data

(60) Provisional application No. 61/296,662, filed on Jan. 20, 2010.

(51) Int. Cl.
*A61F 13/496* (2006.01)
*A61F 13/62* (2006.01)
*A61F 13/45* (2006.01)
*A61F 13/49* (2006.01)

(52) U.S. Cl.
CPC ............ *A61F 13/565* (2013.01); *A61F 13/62* (2013.01); *A61F 13/5655* (2013.01); *A61F 2013/4512* (2013.01); *A61F 2013/49087* (2013.01); *A61F 2013/49098* (2013.01); *A61F 2013/5677* (2013.01); *A61F 2013/5683* (2013.01)

(58) Field of Classification Search
CPC .. A61F 13/622; A61F 13/5655; A61F 13/565; A61F 13/5622; A61F 2013/4512; A61F 2013/49087; A61F 2013/49098; A61F 2013/5677; A61F 2013/5683
USPC ........ 604/385.201, 386, 387, 389, 390, 391, 604/392, 401
See application file for complete search history.

(56) References Cited

U.S. PATENT DOCUMENTS

| | | |
|---|---|---|
| 3,319,307 A | 5/1967 | Marforio |
| 3,475,926 A | 11/1969 | Ruckstuhl |
| 3,577,607 A | 5/1971 | Ikoma et al. |
| 3,638,651 A | 2/1972 | Torr |
| 3,694,867 A | 10/1972 | Stumpf |
| 3,708,833 A | 1/1973 | Ribich et al. |
| 3,842,832 A | 10/1974 | Wideman et al. |
| 3,842,837 A | 10/1974 | Sward |
| 3,848,594 A | 11/1974 | Buell |
| 3,848,597 A | 11/1974 | Endres |
| 3,860,003 A | 1/1975 | Buell |
| 3,911,173 A | 10/1975 | Sprague, Jr. |
| 3,943,981 A | 3/1976 | De Brabander |
| 3,955,575 A | 5/1976 | Okuda |
| 3,994,299 A | 11/1976 | Karami |
| 4,145,763 A | 3/1979 | Abrams et al. |
| 4,205,679 A | 6/1980 | Repke et al. |
| 4,300,967 A | 11/1981 | Sigl |
| 4,322,875 A | 4/1982 | Brown et al. |
| 4,409,049 A | 10/1983 | Passaflume et al. |
| 4,413,623 A | 11/1983 | Pieniak |
| 4,515,595 A | 5/1985 | Kievit et al. |
| 4,518,451 A | 5/1985 | Luceri et al. |
| 4,540,415 A | 9/1985 | Korpman |
| 4,573,986 A | 3/1986 | Minetola et al. |
| 4,595,441 A | 6/1986 | Holvoet et al. |
| 4,596,568 A | 6/1986 | Flug |
| 4,610,678 A | 9/1986 | Weisman et al. |
| 4,610,680 A | 9/1986 | LaFleur |
| 4,610,682 A | 9/1986 | Kopp |
| 4,615,695 A | 10/1986 | Cooper |
| 4,633,565 A | 1/1987 | DeWoskin |
| 4,643,932 A | 2/1987 | Daniels |
| 4,657,802 A | 4/1987 | Morman |
| 4,662,875 A | 5/1987 | Hirotsu et al. |
| 4,663,220 A | 5/1987 | Wisneski et al. |
| 4,673,402 A | 6/1987 | Weisman et al. |
| 4,695,278 A | 9/1987 | Lawson |
| 4,701,179 A | 10/1987 | Kellenberger et al. |
| 4,704,114 A | 11/1987 | Wilson et al. |
| 4,704,115 A | 11/1987 | Buell |
| 4,711,683 A | 12/1987 | Merkatoris |
| 4,761,322 A | 8/1988 | Raley |
| 4,785,996 A | 11/1988 | Ziecker et al. |
| 4,834,735 A | 5/1989 | Alemany et al. |
| 4,834,742 A | 5/1989 | Wilson et al. |
| 4,842,666 A | 6/1989 | Werenicz |
| 4,846,815 A | 7/1989 | Scripps |
| 4,847,134 A | 7/1989 | Fahrenkrug et al. |
| 4,850,989 A | 7/1989 | Villez |
| 4,869,724 A | 9/1989 | Scripps |
| 4,880,423 A | 11/1989 | Green |
| 4,881,997 A | 11/1989 | Hatch |
| 4,884,323 A | 12/1989 | Provost et al. |
| 4,888,231 A | 12/1989 | Angstadt |
| 4,894,060 A | 1/1990 | Nestegard |
| 4,909,803 A | 3/1990 | Aziz et al. |
| 4,909,870 A | 3/1990 | Gould et al. |
| 4,933,224 A | 6/1990 | Hatch |
| 4,936,840 A | 6/1990 | Proxmire |
| 4,938,753 A | 7/1990 | Van Gompel et al. |
| 4,938,757 A | 7/1990 | Van Gompel et al. |
| 4,940,464 A | 7/1990 | Van Gompel et al. |
| 4,946,527 A | 8/1990 | Battrell |
| 4,988,344 A | 1/1991 | Reising et al. |
| 4,988,551 A | 1/1991 | Zegler |
| 4,998,345 A | 3/1991 | Funahashi et al. |
| 4,999,067 A | 3/1991 | Erb et al. |
| 5,000,806 A | 3/1991 | Merkatoris et al. |
| 5,015,245 A | 5/1991 | Noda |
| 5,019,065 A | 5/1991 | Scripps |
| 5,019,073 A | 5/1991 | Roessler et al. |
| 5,032,122 A | 7/1991 | Noel et al. |
| 5,057,097 A | 10/1991 | Gesp |
| 5,058,247 A | 10/1991 | Thomas et al. |
| 5,062,839 A | 11/1991 | Anderson |
| 5,069,678 A | 12/1991 | Yamamoto et al. |
| 5,074,854 A | 12/1991 | Davis |
| 5,087,253 A | 2/1992 | Cooper |
| 5,106,385 A | 4/1992 | Allen et al. |
| 5,125,246 A | 6/1992 | Shytles |
| 5,147,345 A | 9/1992 | Young et al. |
| 5,147,487 A | 9/1992 | Nomura et al. |
| 5,151,092 A | 9/1992 | Buell et al. |
| 5,163,932 A | 11/1992 | Nomura |
| 5,167,897 A | 12/1992 | Weber et al. |
| 5,176,670 A | 1/1993 | Roessler et al. |
| 5,221,274 A | 6/1993 | Buell et al. |
| 5,234,423 A | 8/1993 | Alemany et al. |
| 5,242,436 A | 9/1993 | Weil et al. |
| 5,246,433 A | 9/1993 | Hasse et al. |
| 5,246,656 A | 9/1993 | Stephenson et al. |
| 5,269,776 A | 12/1993 | Lancaster et al. |
| 5,296,080 A | 3/1994 | Merkatoris et al. |
| 5,326,612 A | 7/1994 | Goulait |
| 5,330,458 A | 7/1994 | Buell et al. |
| 5,358,500 A | 10/1994 | LaVon et al. |
| 5,366,452 A | 11/1994 | Widlund et al. |
| 5,370,634 A | 12/1994 | Ando et al. |
| 5,374,262 A | 12/1994 | Keuhn, Jr. et al. |

(56) References Cited

U.S. PATENT DOCUMENTS

| | | |
|---|---|---|
| 5,380,313 A | 1/1995 | Goulait et al. |
| 5,399,177 A | 3/1995 | Blaney et al. |
| 5,399,219 A | 3/1995 | Roessler et al. |
| 5,417,789 A | 5/1995 | Lauritzen |
| 5,454,803 A | 10/1995 | Sageser et al. |
| 5,460,622 A | 10/1995 | Dragoo et al. |
| 5,462,540 A | 10/1995 | Caldwell |
| 5,476,458 A | 12/1995 | Glaug et al. |
| 5,496,298 A | 3/1996 | Kuepper et al. |
| 5,496,428 A | 3/1996 | Sageser et al. |
| 5,527,302 A | 6/1996 | Endres et al. |
| 5,531,732 A | 7/1996 | Wood |
| 5,542,943 A | 8/1996 | Sageser |
| 5,554,145 A | 9/1996 | Roe et al. |
| 5,569,234 A | 10/1996 | Buell |
| 5,575,784 A | 11/1996 | Ames-Ooten et al. |
| 5,576,090 A | 11/1996 | Suzuki |
| 5,577,540 A | 11/1996 | Sageser |
| 5,580,411 A | 12/1996 | Nease et al. |
| 5,591,155 A | 1/1997 | Nishikawa et al. |
| 5,595,567 A | 1/1997 | King et al. |
| 5,624,420 A | 4/1997 | Bridges et al. |
| 5,624,427 A | 4/1997 | Bergman et al. |
| 5,624,428 A | 4/1997 | Sauer |
| H1674 H | 8/1997 | Ames |
| 5,662,638 A | 9/1997 | Johnson et al. |
| 5,669,996 A | 9/1997 | Jessup |
| 5,683,533 A | 11/1997 | Keighley et al. |
| 5,685,873 A | 11/1997 | Bruemmer |
| 5,685,874 A | 11/1997 | Buell et al. |
| 5,693,165 A | 12/1997 | Schmitz |
| 5,695,488 A | 12/1997 | Sosalla |
| 5,705,013 A | 1/1998 | Nease et al. |
| 5,722,127 A | 3/1998 | Coates |
| 5,722,968 A | 3/1998 | Datta et al. |
| 5,725,714 A | 3/1998 | Fujioka et al. |
| 5,735,840 A | 4/1998 | Kline et al. |
| 5,746,730 A | 5/1998 | Suzuki et al. |
| 5,776,123 A | 7/1998 | Goerg et al. |
| 5,779,831 A | 7/1998 | Schmitz |
| 5,830,206 A | 11/1998 | Larsson |
| 5,836,931 A | 11/1998 | Toyoda et al. |
| 5,846,262 A | 12/1998 | Sayama et al. |
| 5,846,365 A | 12/1998 | Kline et al. |
| 5,853,405 A | 12/1998 | Suprise |
| 5,855,574 A | 1/1999 | Kling et al. |
| 5,873,868 A | 2/1999 | Nakahata |
| 5,873,870 A | 2/1999 | Seitz et al. |
| 5,897,545 A | 4/1999 | Kline et al. |
| 5,899,895 A | 5/1999 | Robles et al. |
| 5,899,896 A | 5/1999 | Suprise |
| 5,928,212 A | 7/1999 | Kline et al. |
| 5,957,908 A | 9/1999 | Kline et al. |
| 5,961,761 A | 10/1999 | Heindel et al. |
| 6,004,306 A | 12/1999 | Robles et al. |
| 6,030,373 A | 2/2000 | VanGompel et al. |
| 6,120,489 A | 9/2000 | Johnson |
| 6,142,985 A | 11/2000 | Feist |
| 6,149,639 A | 11/2000 | Lundberg et al. |
| 6,210,388 B1 | 4/2001 | Widlund et al. |
| RE37,154 E | 5/2001 | Nomura et al. |
| 6,230,374 B1 | 5/2001 | Widlund |
| 6,240,569 B1 | 6/2001 | Van Gompel |
| 6,273,165 B1 | 8/2001 | Gunderson et al. |
| 6,328,725 B2 | 12/2001 | Femfors |
| 6,340,782 B1 | 1/2002 | Kling et al. |
| 6,375,646 B1 | 4/2002 | Widlund |
| 6,428,526 B1 | 8/2002 | Heindel et al. |
| 6,447,628 B1 | 9/2002 | Couillard et al. |
| 6,454,752 B1 | 9/2002 | Huang et al. |
| 6,461,344 B1 | 10/2002 | Widlund et al. |
| 6,491,676 B1 | 12/2002 | Suzuki et al. |
| 6,494,872 B1 | 12/2002 | Suzuki et al. |
| 6,524,293 B1 | 2/2003 | Elsberg et al. |
| 6,534,694 B2 | 3/2003 | Kling et al. |
| 6,579,275 B1 | 6/2003 | Pozniak et al. |
| 6,872,267 B2 | 3/2005 | Popp et al. |
| 6,972,012 B1 | 12/2005 | Pozniak et al. |
| 6,994,698 B2 | 2/2006 | Leak et al. |
| 7,056,313 B2 | 6/2006 | Franke et al. |
| 7,150,730 B2 | 12/2006 | Hasler et al. |
| 7,300,427 B2 | 11/2007 | Sugito et al. |
| 7,371,302 B2 | 5/2008 | Miyamoto et al. |
| 7,473,818 B2 | 1/2009 | Datta et al. |
| 7,524,313 B2 | 4/2009 | Kline et al. |
| 7,717,896 B2 | 5/2010 | Otsubo et al. |
| 7,806,880 B2 | 10/2010 | Roe et al. |
| 7,988,682 B2 | 8/2011 | Olsson et al. |
| 8,147,586 B2 | 4/2012 | Johnson et al. |
| 8,430,858 B2 | 4/2013 | Back |
| 2002/0188268 A1 | 12/2002 | Kline et al. |
| 2008/0065042 A1 | 3/2008 | Wood et al. |
| 2008/0097363 A1 | 4/2008 | Fernfors et al. |
| 2008/0125736 A1 | 5/2008 | Kline et al. |
| 2011/0178485 A1 | 7/2011 | LaVon et al. |

FOREIGN PATENT DOCUMENTS

| | | |
|---|---|---|
| EP | 0 417 766 A1 | 3/1991 |
| EP | 0 433 951 A2 | 6/1991 |
| EP | 0 455 231 A1 | 11/1991 |
| EP | 0 456 281 A2 | 11/1991 |
| EP | 0 528 282 A3 | 2/1993 |
| EP | 0 532 034 A2 | 3/1993 |
| EP | 0 567 792 A1 | 3/1993 |
| EP | 0 570 980 B1 | 11/1993 |
| EP | 0 587 196 A1 | 3/1994 |
| EP | 0 589 859 A1 | 3/1994 |
| EP | 0 597 331 A1 | 5/1994 |
| EP | 0 600 494 A1 | 6/1994 |
| EP | 0 605 012 A1 | 7/1994 |
| EP | 0 605 013 A1 | 7/1994 |
| EP | 0 700 675 A1 | 3/1996 |
| EP | 0 743 052 A2 | 11/1996 |
| FR | 2 606 257 | 5/1988 |
| GB | 2 244 422 | 4/1991 |
| GB | 2 245 149 A | 1/1992 |
| GB | 2 267 024 A | 11/1993 |
| GB | 2 285 208 A1 | 7/1995 |
| GB | 2 308 290 A | 6/2007 |
| JP | 59-129805 A1 | 8/1984 |
| JP | 62-069804 | 3/1987 |
| JP | 62-125002 | 6/1987 |
| JP | 62-162001 | 7/1987 |
| JP | 62-162002 | 7/1987 |
| JP | 63-120102 | 5/1988 |
| JP | 63-243307 | 10/1988 |
| JP | 63-243308 | 10/1988 |
| JP | 01-168905 A | 7/1989 |
| JP | 02-004367 | 1/1990 |
| JP | 04-005826 U | 5/1990 |
| JP | 04-007819 | 5/1991 |
| JP | 03-176053 | 7/1991 |
| JP | 03-195555 | 8/1991 |
| JP | 04-028364 | 1/1992 |
| JP | 04-035663 | 2/1992 |
| JP | 04-044920 | 4/1992 |
| JP | 04-144558 | 5/1992 |
| JP | 04-161152 | 6/1992 |
| JP | 04-261655 | 9/1992 |
| JP | 04-354948 | 12/1992 |
| JP | 05-31135 | 2/1993 |
| JP | 05-76566 | 3/1993 |
| JP | 1993-039531 U | 5/1993 |
| JP | 05-137746 | 6/1993 |
| JP | 1993-317356 | 12/1993 |
| JP | 06-000204 | 1/1994 |
| JP | 06-005562 | 1/1994 |
| JP | 06-114084 | 4/1994 |
| JP | 06-055623 U | 8/1994 |
| JP | 06-296643 | 10/1994 |
| JP | 1994-285113 A | 10/1994 |
| JP | 1994-077719 U | 11/1994 |
| JP | 07-75653 | 3/1995 |

(56) References Cited

FOREIGN PATENT DOCUMENTS

| | | |
|---|---|---|
| JP | 07-80023 | 3/1995 |
| JP | 07-252762 | 10/1995 |
| JP | 30-24003 U | 2/1996 |
| JP | 08-56986 | 3/1996 |
| JP | 08-56988 | 3/1996 |
| JP | 2006-055669 A | 3/2006 |
| TW | 261765 | 1/1995 |
| WO | WO 90/07313 A1 | 7/1990 |
| WO | WO 91/08725 A1 | 6/1991 |
| WO | WO 92/20251 | 11/1992 |
| WO | WO 93/24085 A1 | 12/1993 |
| WO | WO 95/00096 A1 | 1/1995 |
| WO | WO 95/03765 A3 | 2/1995 |
| WO | WO 95/05140 A1 | 2/1995 |
| WO | WO 95/12491 A1 | 5/1995 |
| WO | WO 95/13775 A1 | 5/1995 |
| WO | WO 95/19753 A1 | 7/1995 |
| WO | WO 95/22951 A1 | 8/1995 |
| WO | WO 95/27460 A1 | 10/1995 |
| WO | WO 95/27462 A1 | 10/1995 |
| WO | WO 95/27463 A1 | 10/1995 |
| WO | WO 95/29657 A1 | 11/1995 |
| WO | WO 95/32695 A1 | 12/1995 |
| WO | WO 95/32696 A1 | 12/1995 |
| WO | WO 95/34266 A1 | 12/1995 |
| WO | WO 96/05788 A1 | 2/1996 |
| WO | WO 96/14815 A1 | 5/1996 |
| WO | WO 96/19960 A1 | 7/1996 |
| WO | WO 96/24319 A1 | 8/1996 |
| WO | WO 96/31179 A2 | 10/1996 |
| WO | WO 96/35402 A1 | 11/1996 |
| WO | WO 97/02796 A1 | 1/1997 |
| WO | WO 97/02799 A1 | 1/1997 |
| WO | WO 97/09953 A1 | 3/1997 |
| WO | WO 97/16146 A1 | 5/1997 |
| WO | WO 97/18785 A1 | 5/1997 |
| WO | WO 97/28774 A1 | 8/1997 |
| WO | WO 97/30671 A2 | 8/1997 |
| WO | WO 97/32552 A1 | 9/1997 |
| WO | WO 97/34555 A1 | 9/1997 |
| WO | WO 97/34556 A2 | 9/1997 |
| WO | WO 97/46197 A1 | 12/1997 |

OTHER PUBLICATIONS

Written Opinion, PCT/US2011/021828 date of mailing Aug. 2, 2011.
All Office Actions, Responses and Claims for U.S. Appl. No. 13/010,040.
All Office Actions, Responses and Claims for U.S. Appl. No. 13/010,052.
All Office Actions, Responses and Claims for U.S. Appl. No. 13/010,062.
All Office Actions, Responses and Claims for U.S. Appl. No. 13/010,072.
All Office Actions, Responses and Claims for U.S. Appl. No. 13/010,083.
Opposition Division, European Patent Office, Decision to Maintain the European Patent in Amended Form (Application No. 97916081.9-2314/0959855), dated Jun. 20, 2007.
European Patent Office, Grounds for the decision (Annex) (Application No. 97 916 087.9).
Graham Boon, Elkington and Fife LLP, Response to Notice of Opposition (European Patent Application No. 97916081.9), dated Mar. 18, 2004.
Graham Boon, Elkington and Fife LLP, Grounds of Appeal on Behalf of the Patentee (Appeal Case No. T0489/05-326), dated Jul. 4, 2005.
European Patent Office, Notice of Opposition to a European Patent, Patent No. EP 0959855 Bl, dated Nov. 27, 2002.
C. R. Davies, Frank B. Dehn & Co., Notice of Opposition and Statement of Facts and Arguments (in re: European Patent No. 0959855B1), dated Aug. 27, 2003.
Photographs labeled "L-78338-00/LB-858 Huggies Supreme STEP 4 (Readi II)", 8 pages.
Albihns, Notice of Opposition (in re: European Patent EP-B-0 959 855), dated Aug. 21, 2003.
RCE for U.S. Appl. No. 13/929,900, dated Mar. 14, 2016.
Notice of Allowance for U.S. Appl. No. 13/929,900, dated Dec. 14, 2015.
Amendment for U.S. Appl. No. 13/929,900, dated Nov. 19, 2015.
Non-Final Rejection for U.S. Appl. No. 13/929,900, dated Aug. 19, 2015.
Non-Final Rejection for U.S. Appl. No. 13/929,970, dated Jan. 15, 2016.

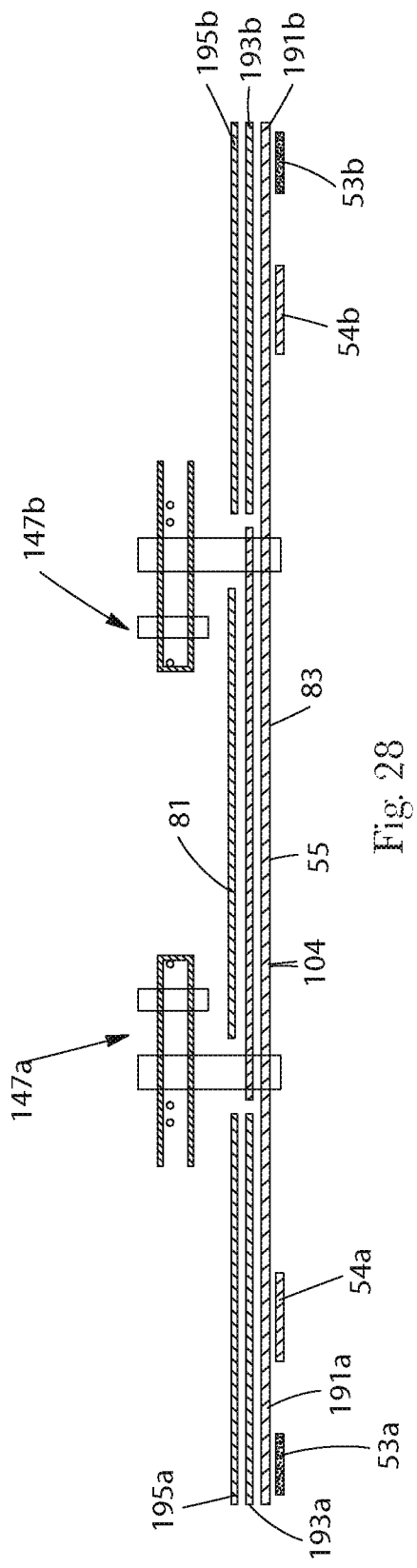
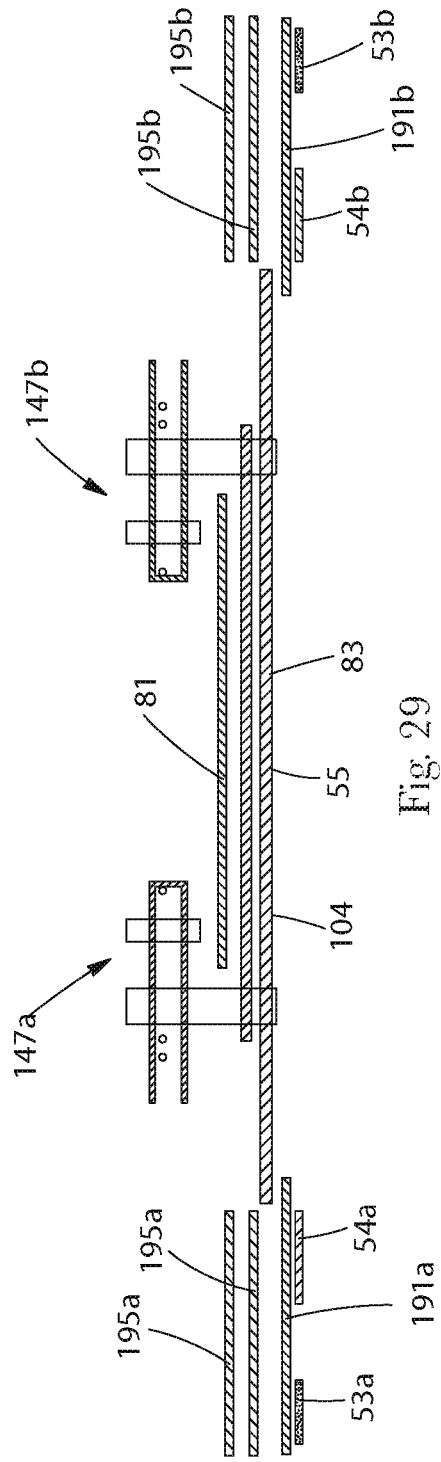

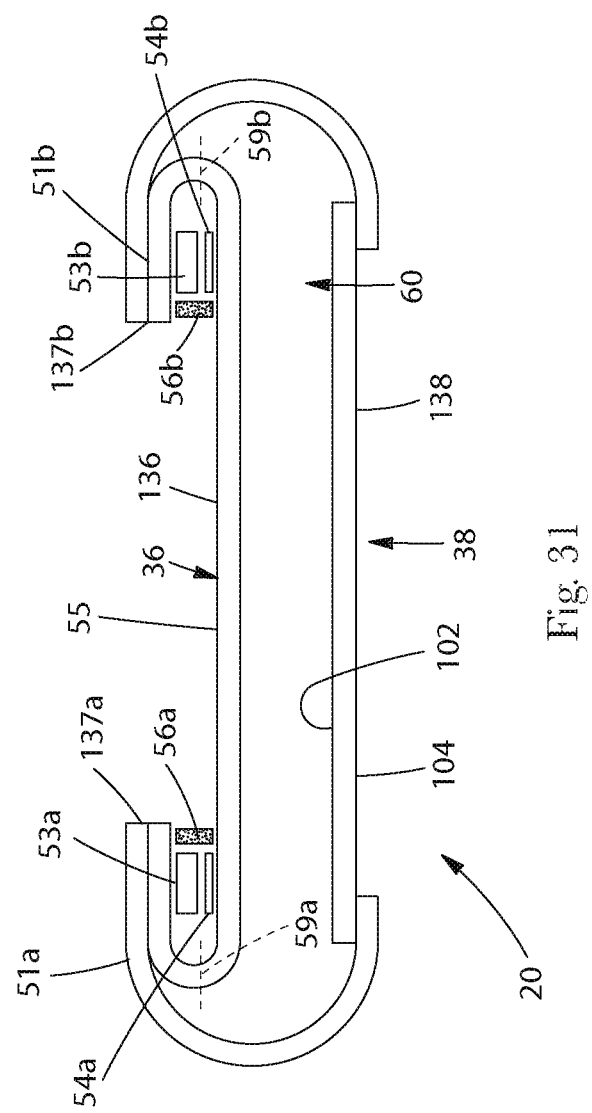

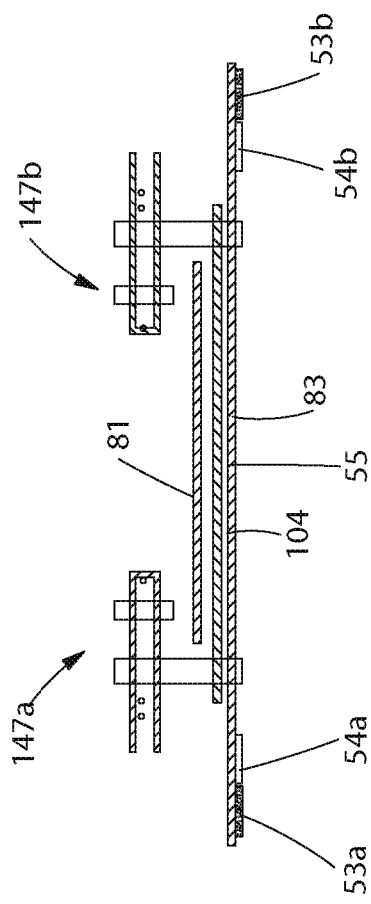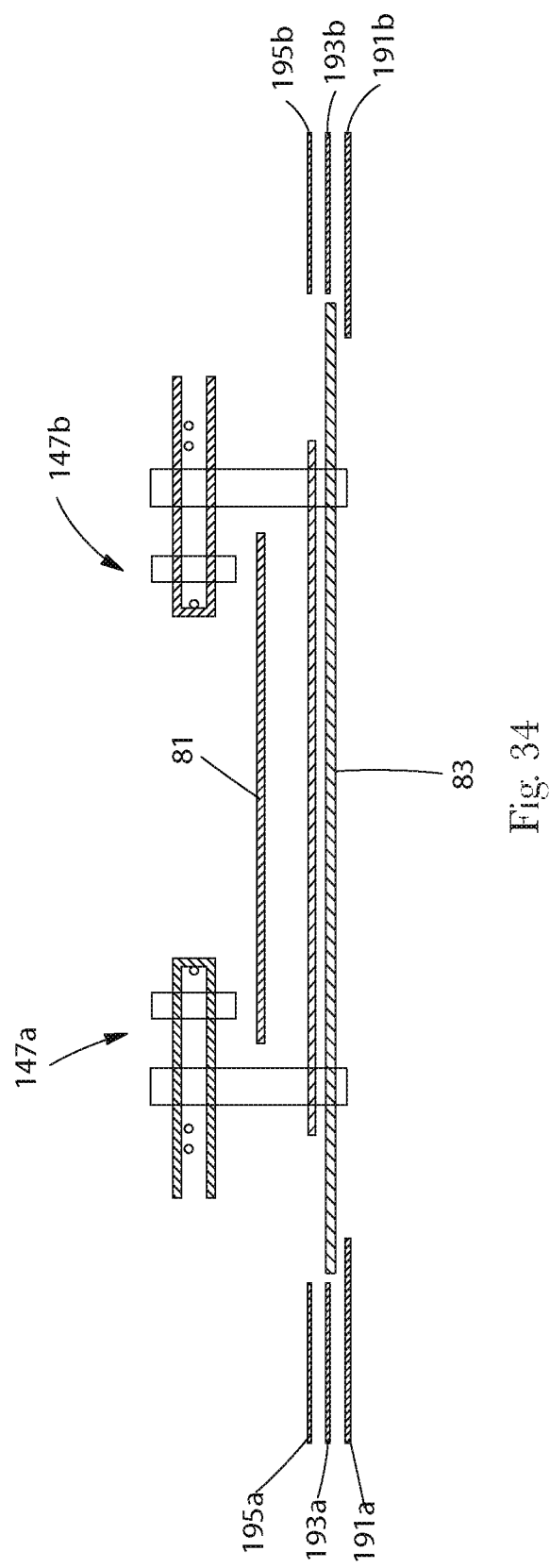

REFASTENABLE ABSORBENT ARTICLE

CROSS REFERENCE TO RELATED APPLICATION

This application is a continuation of, and claims priority under 35 U.S.C. §120 to, U.S. patent application Ser. No. 13/010,040, filed on Jan. 20, 2011, which claims the benefit, under 35 USC §119(e), of U.S. Provisional Patent Application Ser. No. 61/296,662, filed on Jan. 20, 2010, the entire disclosures of which are fully incorporated by reference herein.

FIELD

The present disclosure generally relates to absorbent articles and methods for manufacturing the same, and more particularly relates to refastenable and disposable absorbent articles and methods of manufacturing the same.

BACKGROUND

Many refastenable pull-on disposable absorbent articles, such as pants or diapers, for example, are provided to a consumer with fastening components initially engaged. In such structures, where first and second fasteners or a first fastener and a second fastener, for example, are initially engaged, the fastening components may form a pant comprising two side seams, a waist opening, and two leg openings. Consumers generally prefer that the side seams of the pant be easily openable and reliably recloseable. Initially engaged fastening components, if designed to deliver a low initial opening force, may also have a low subsequent opening force after re-closing of the side seams. The side seam reopening force of an opened and re-closed side seam (i.e., fasteners) is likely to require a lower force than the initial opening force. Pants with a low subsequent side seam opening force may lead to poor side seam strength and a less secure closure, since the same fasteners provide not only the initial, preferably low opening force, but also must provide adequate side seam strength after refastening. What is needed is an improvement over the foregoing.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

In the drawing and in the written description, lowercase letters appended to reference numerals indicate generally symmetric elements, e.g., left and right symmetric elements may be respectively identified by the reference numerals 1*a* and 1*b*. A reference numeral without an appended lowercase letter identifies all of the elements to which that particular reference numeral applies, unless otherwise indicated herein.

Common elements of various figures may not be numbered in all figures for simplicity. Applicants reserve the right to rely on the specification and other figures of the specification for support. While common numbers may be used to denote particular elements in various figures, it will be understood that although an element has as a common number, the element could be an alternative embodiment (i.e., the same number does not necessarily mean the element is the same, although the element could be the same).

Figure 1:
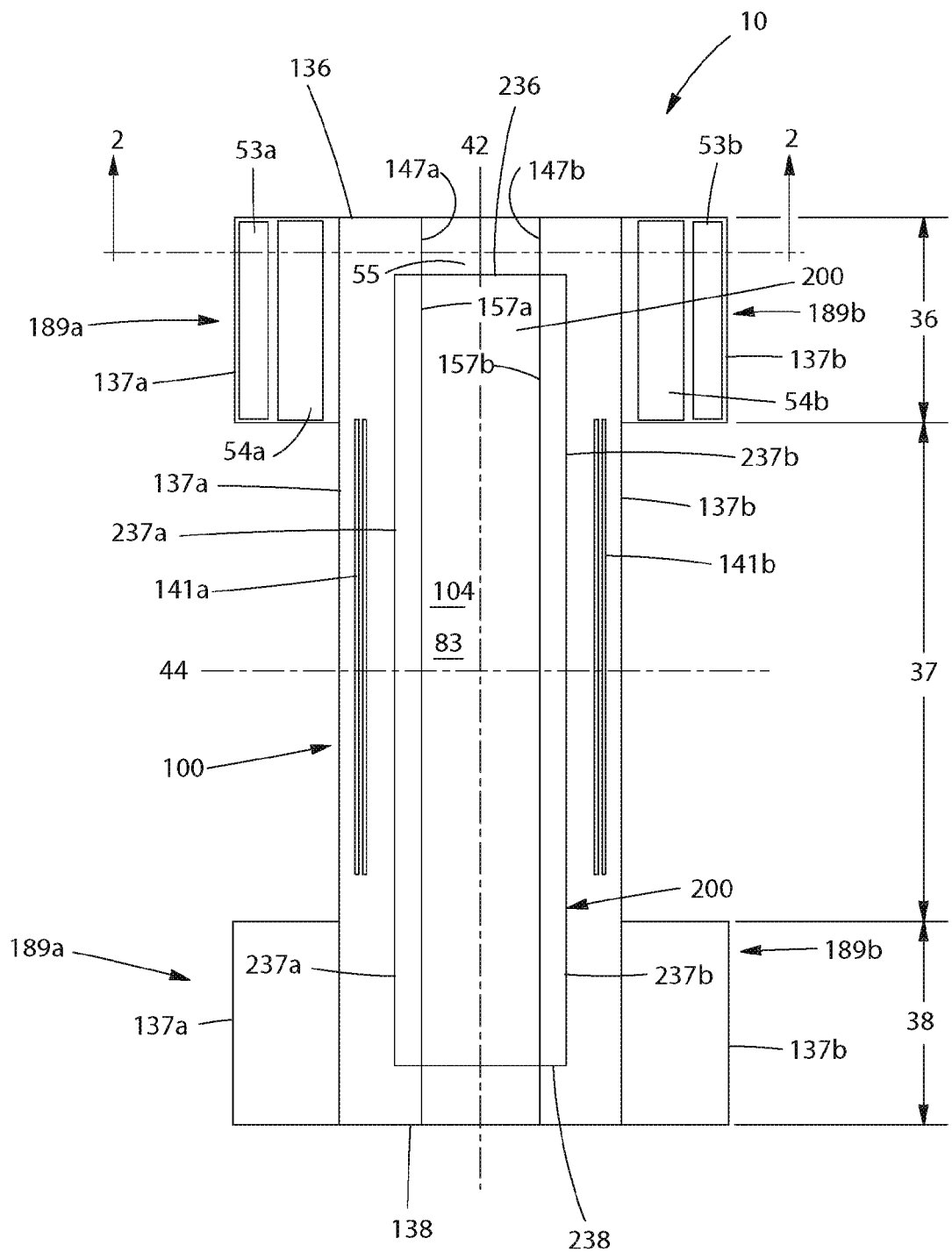

FIG. 1 is a plan view of a simplified absorbent article shown in its flat, uncontracted state prior to being formed into a pant in accordance with one non-limiting embodiment. In FIG. 1, the exterior surface of the absorbent article is shown facing the viewer.

Figure 2:
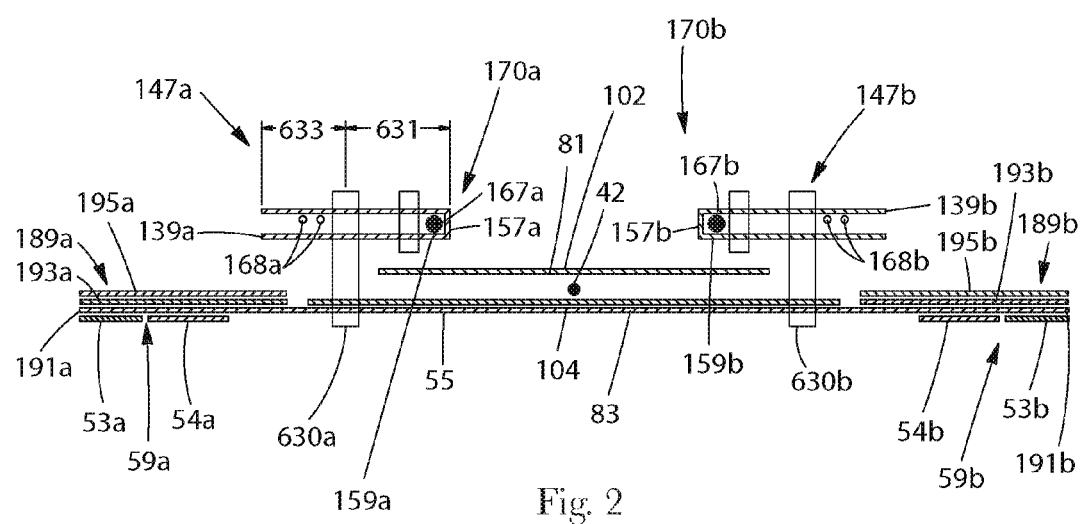

FIG. 2 is a cross-sectional view of the absorbent article of FIG. 1, taken along line A-A in accordance with one non-limiting embodiment.

Figure 3:
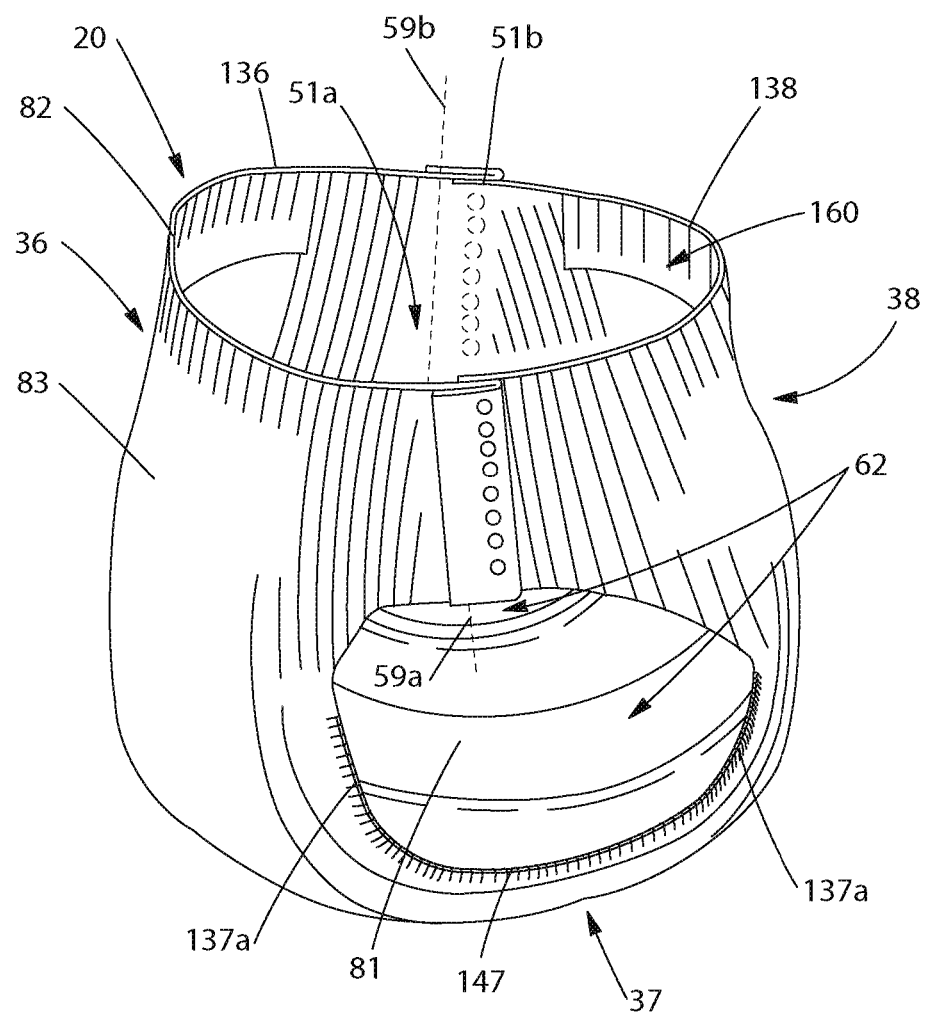

FIG. 3 is a perspective view of a pant formed from the absorbent article of FIG. 1 joined by permanent side edge seams in accordance with one non-limiting embodiment.

Figure 4:
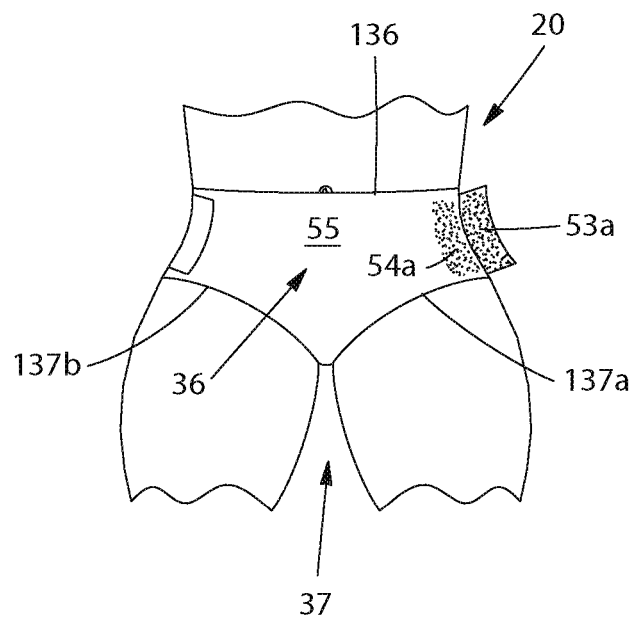

FIG. 4 is a front elevation view of a pant being worn about a lower torso of a wearer in accordance with one non-limiting embodiment.

Figure 5:
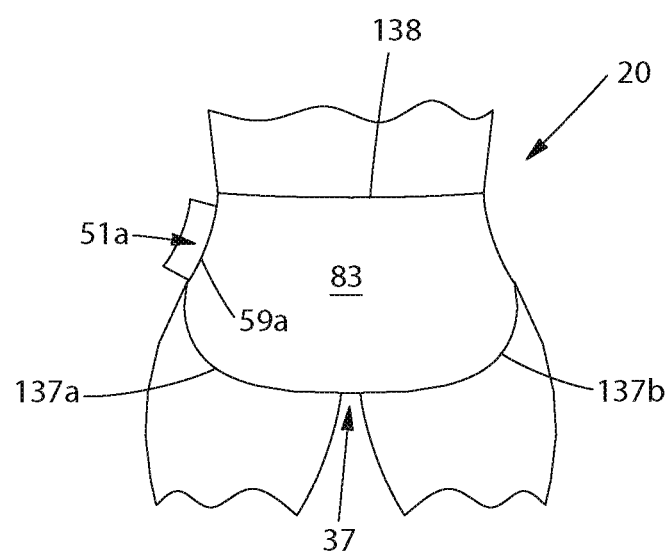

FIG. 5 is a rear elevation view of the pant of FIG. 4 in accordance with one non-limiting embodiment.

Figure 6:
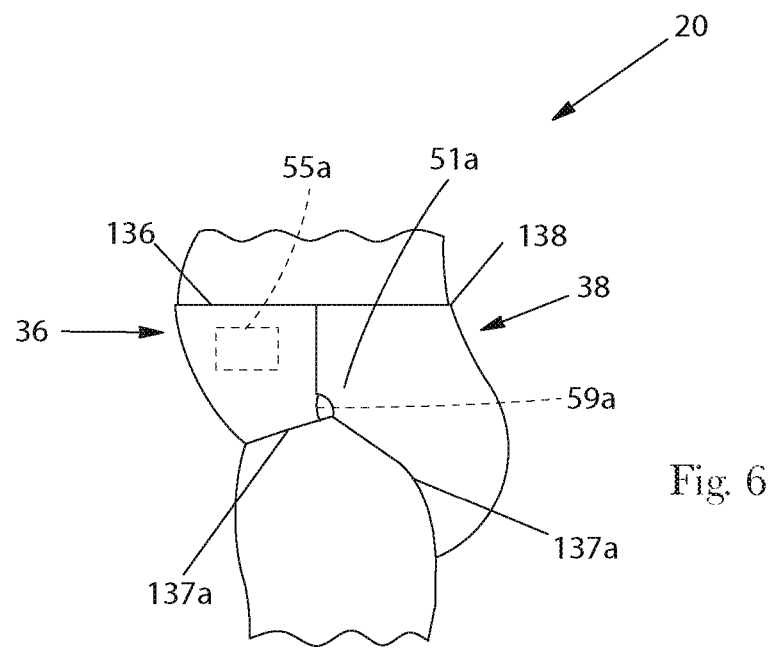

FIG. 6 is a left side elevation view of the pant of FIG. 4 in accordance with one non-limiting embodiment.

Figure 7:
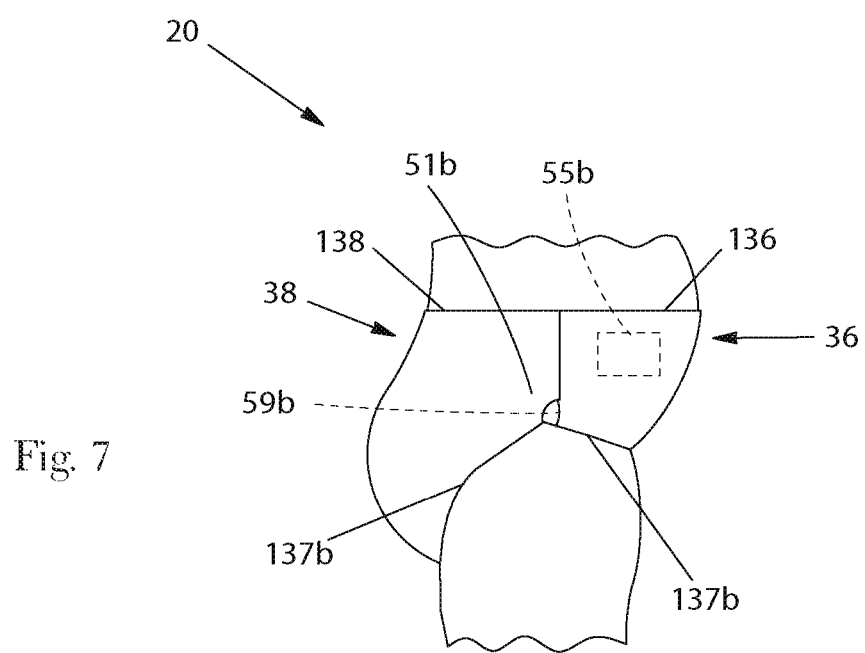

FIG. 7 is a right side elevation view of the pant of FIG. 4 in accordance with one non-limiting embodiment.

Figure 8:
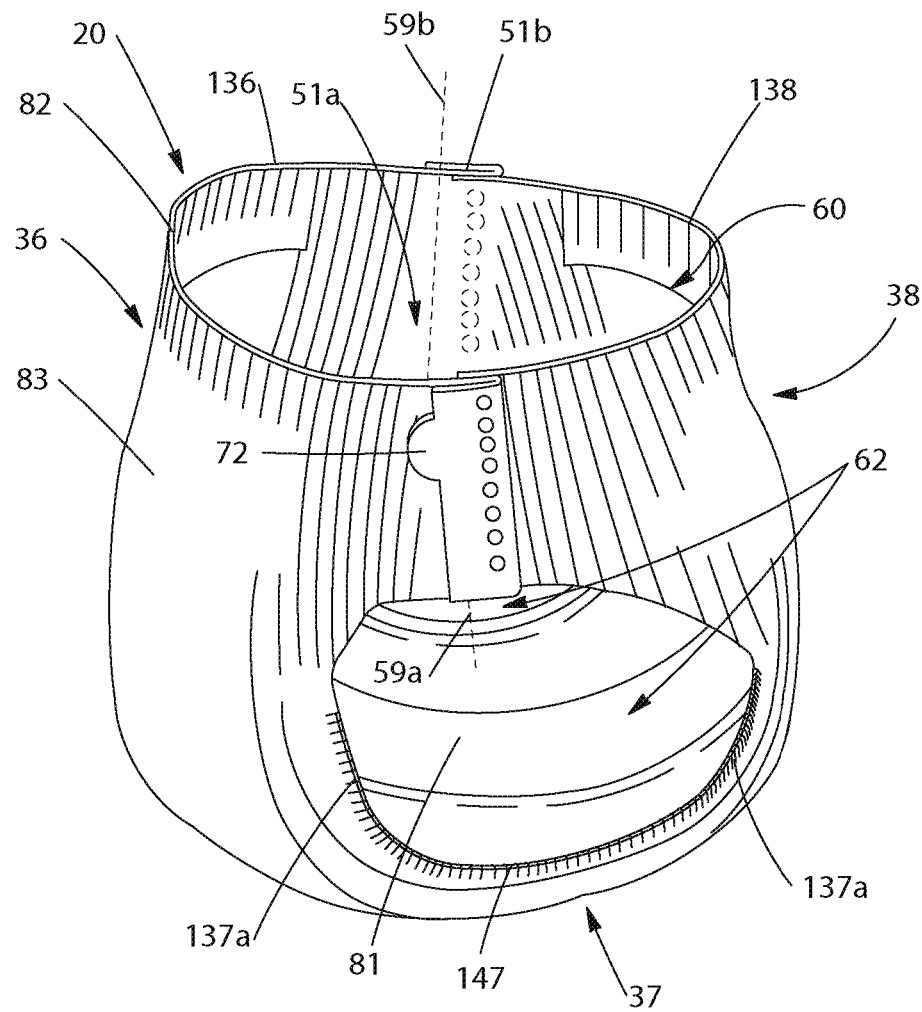

FIG. 8 is a perspective view of a pant joined by a permanent side edge seam in accordance with one non-limiting embodiment.

Figure 9:
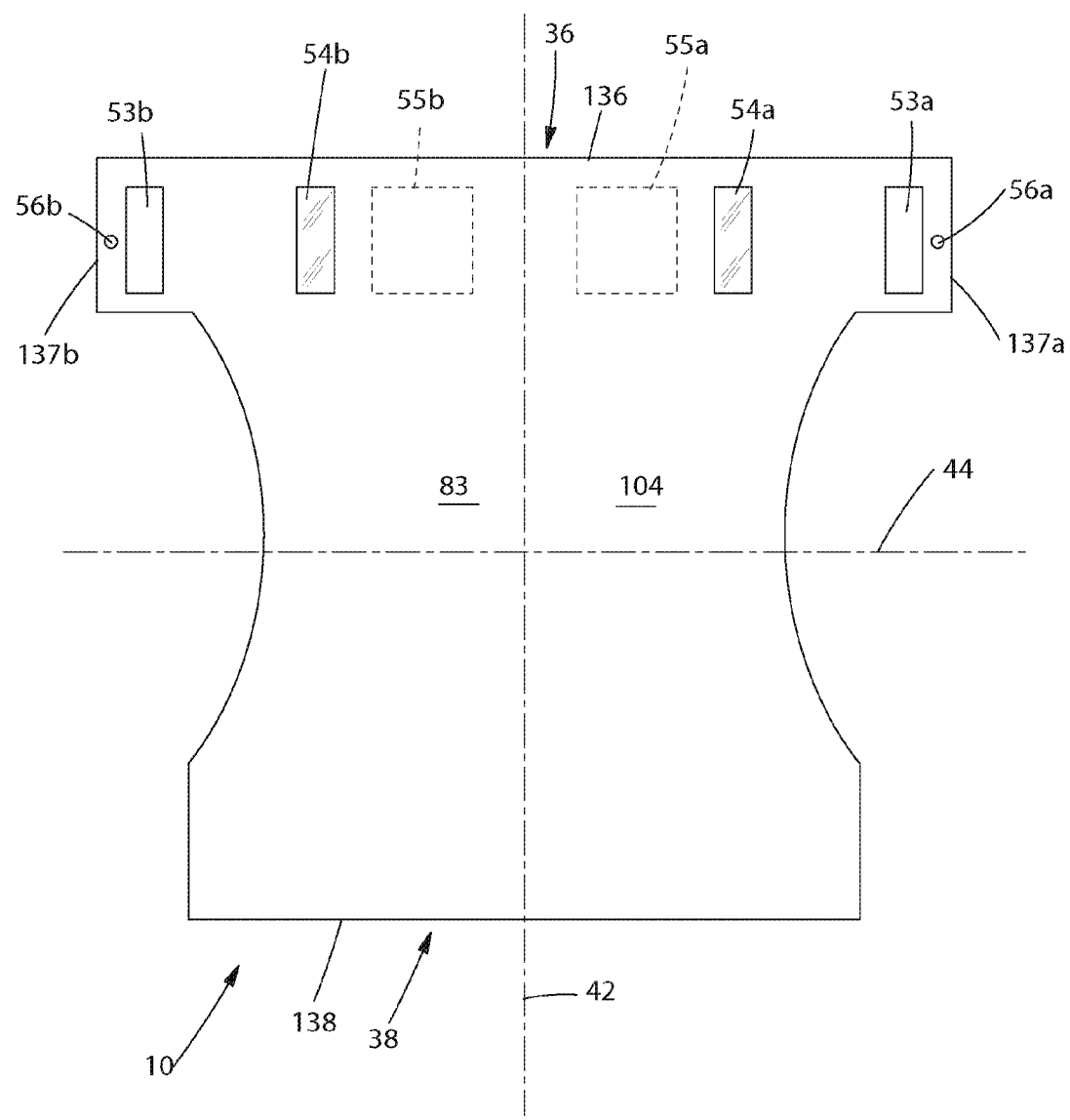

FIG. 9 is a plan view of a simplified absorbent article shown in a flat, uncontracted state and configured to be formed into a pant comprising a flange seam in accordance with one non-limiting embodiment.

Figure 10:
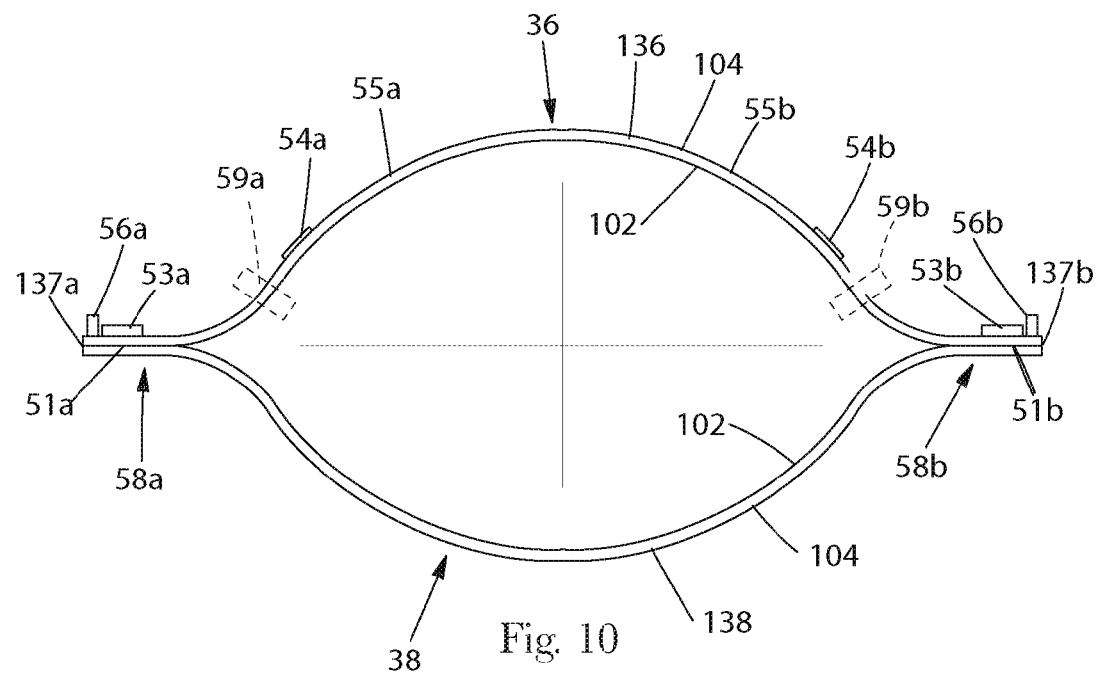

FIG. 10 is a top view of the simplified absorbent article of FIG. 9 partially formed into the pant in accordance with one non-limiting embodiment.

Figure 11:
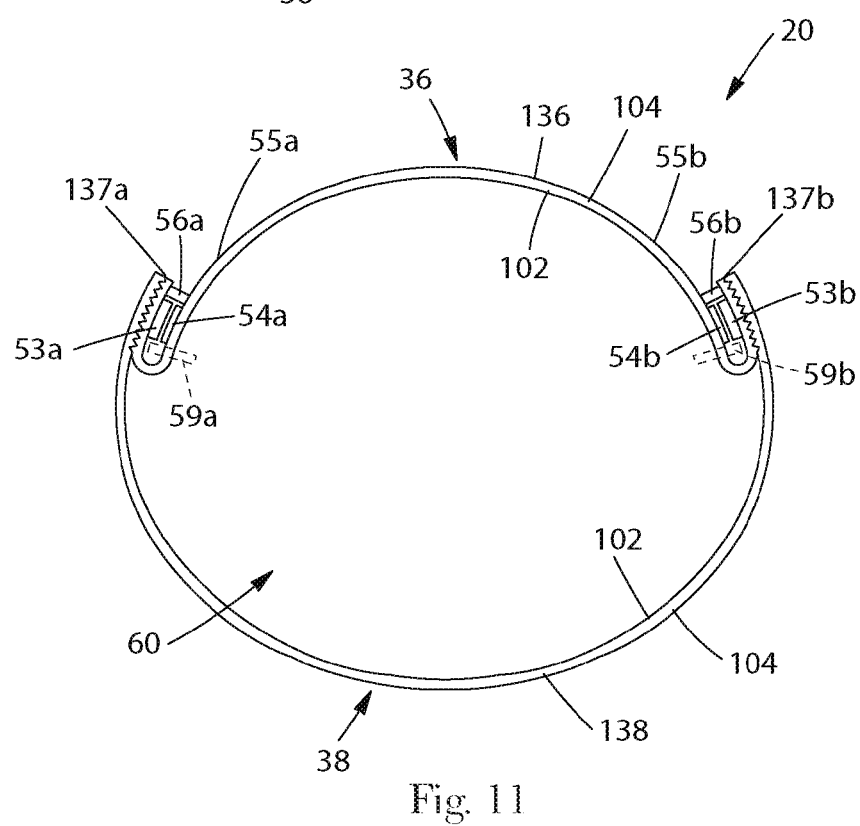

FIG. 11 is a top view of the simplified absorbent article of FIG. 9 formed into the pant in accordance with one non-limiting embodiment.

Figure 12:
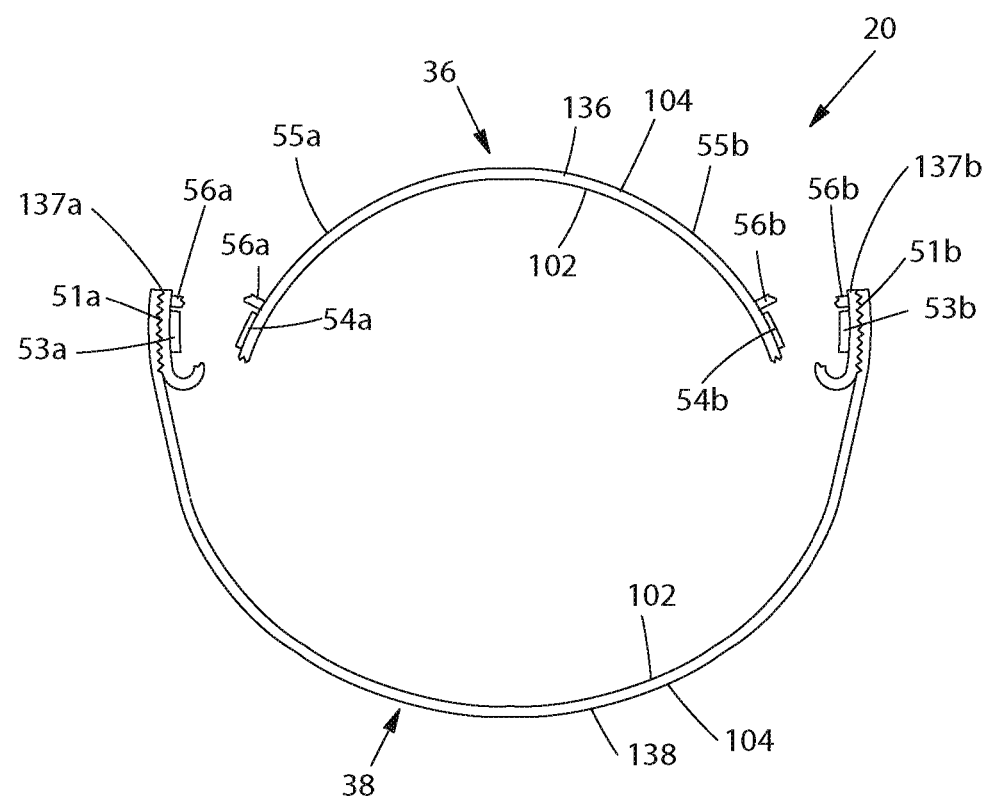

FIG. 12 is a top view of the simplified pant of FIG. 11 with separation zones separated in accordance with one non-limiting embodiment.

Figure 13:
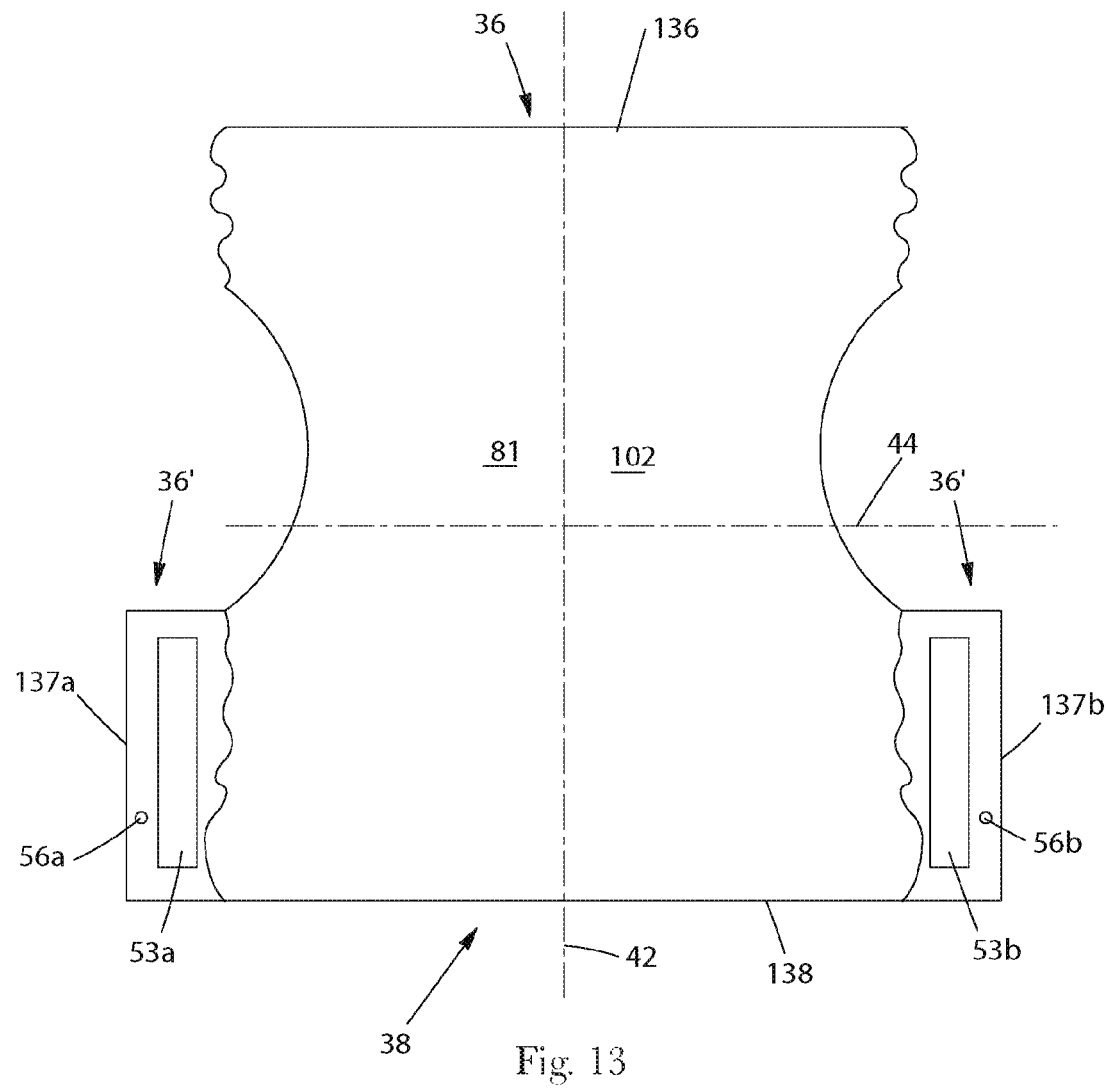

FIG. 13 is a plan view of the simplified pant of FIG. 12 in a flat, uncontracted state in accordance with one non-limiting embodiment.

Figure 14:
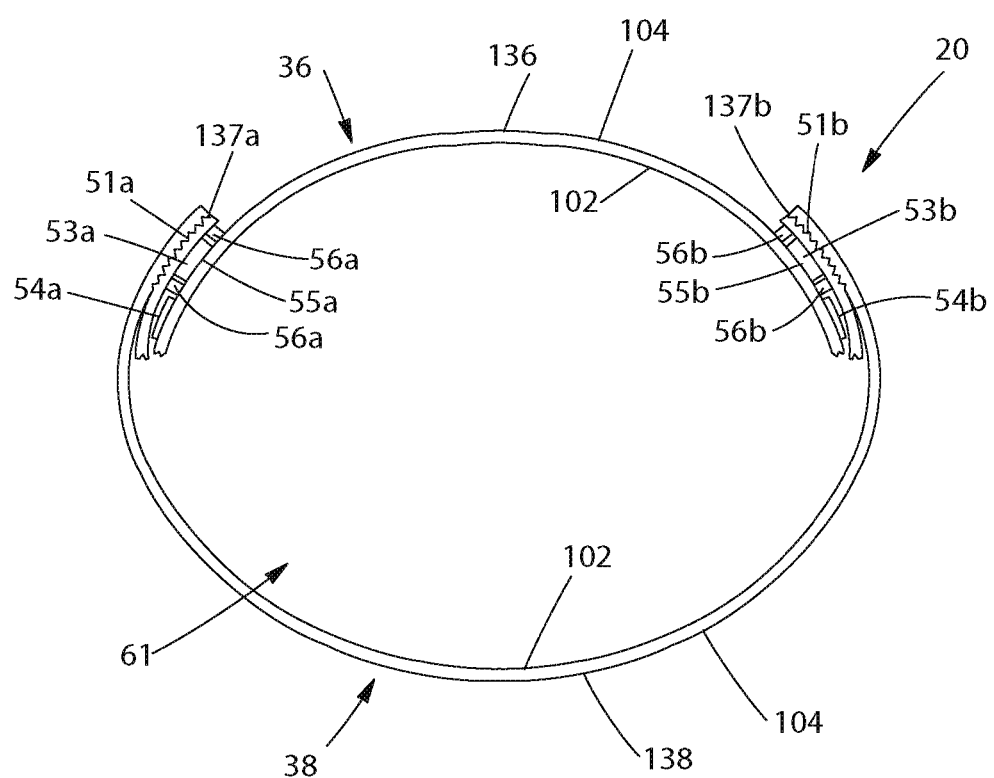

FIG. 14 is a top view of the simplified pant of FIG. 12 with the separation zones separated and first fastening components refastened to a second fastening component that is a part of, formed with, disposed on, or attached to a portion of front waist region of the pant in accordance with one non-limiting embodiment.

Figure 15:
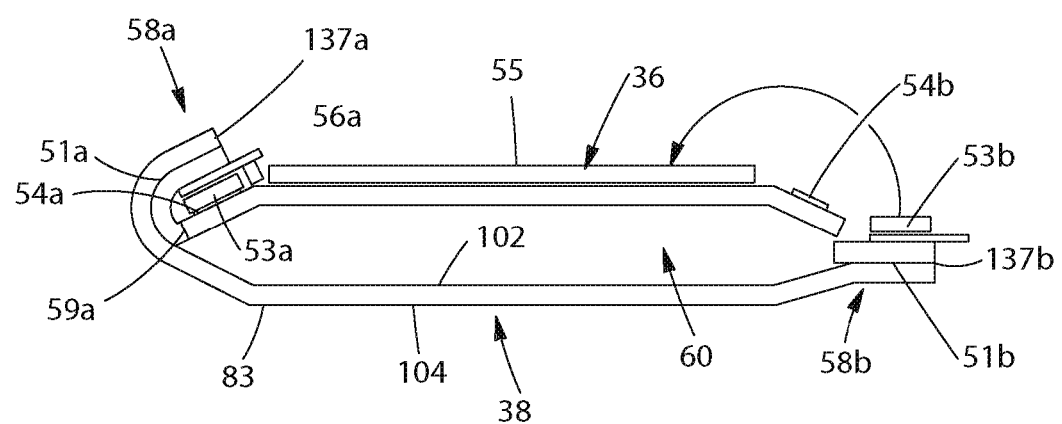

FIG. 15 is a top view of a pant formed with a flange seam in accordance with one non-limiting embodiment.

Figure 16:
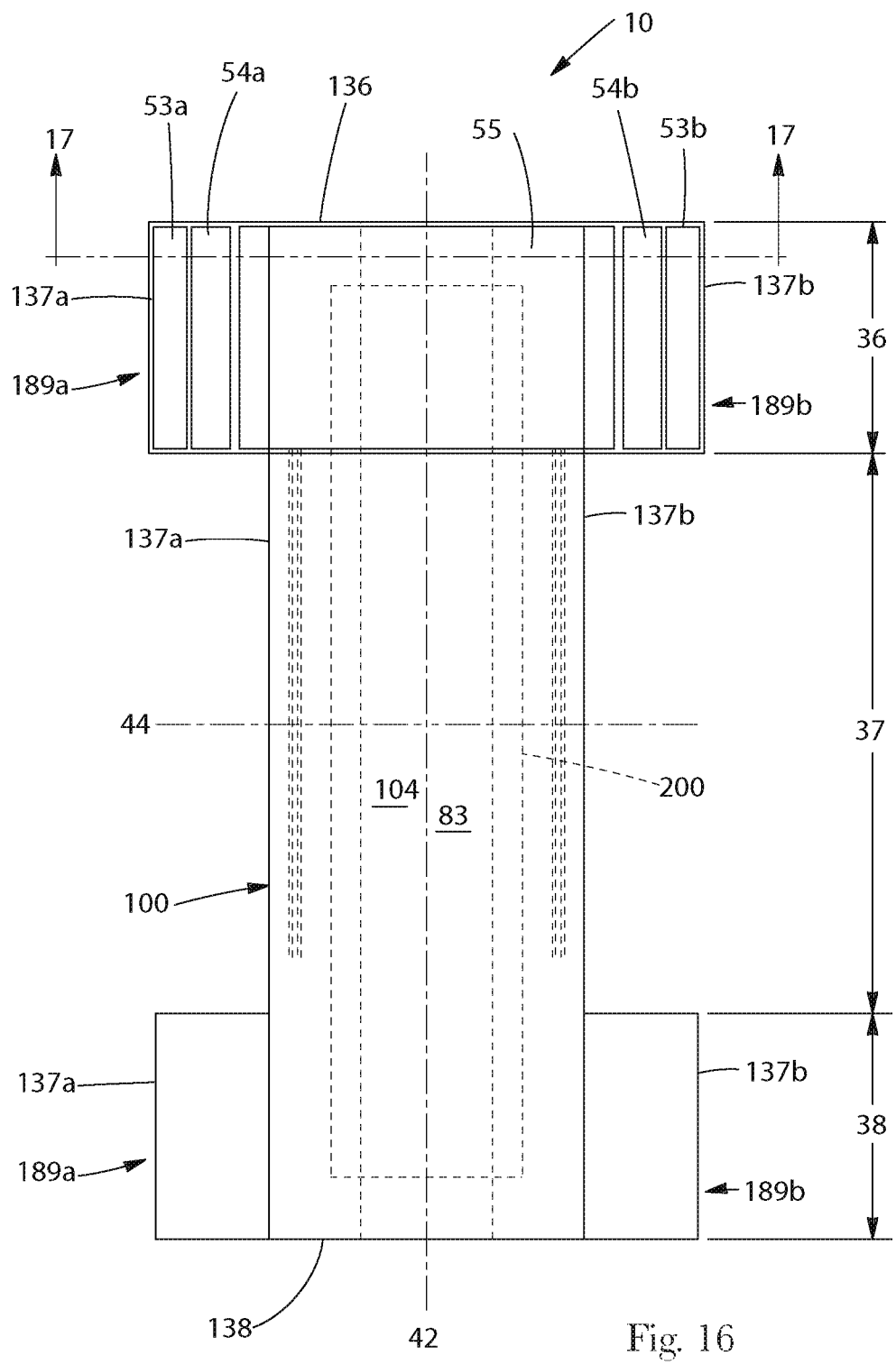

FIG. 16 is a plan view of a simplified absorbent article shown in its flat, uncontracted state prior to being formed into a pant in accordance with one non-limiting embodiment. In FIG. 16, the exterior surface of the absorbent article is shown facing the viewer.

Figure 17:
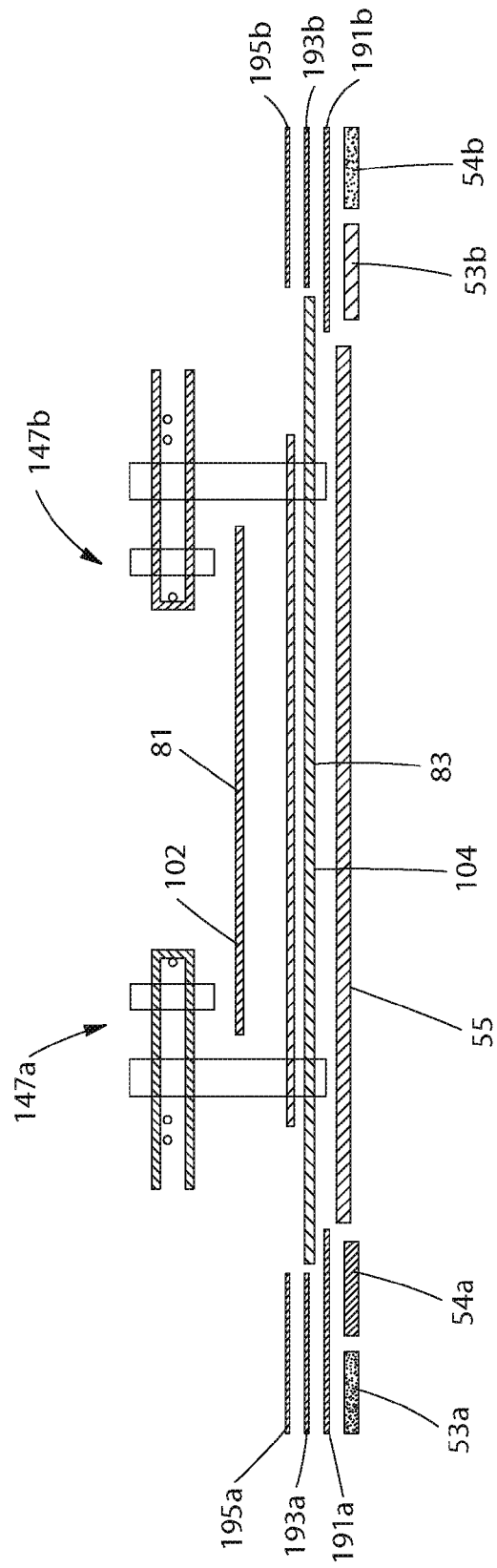

FIG. 17 is a cross-sectional view of the absorbent article of FIG. 16, taken along line A-A in accordance with one non-limiting embodiment.

Figure 18:
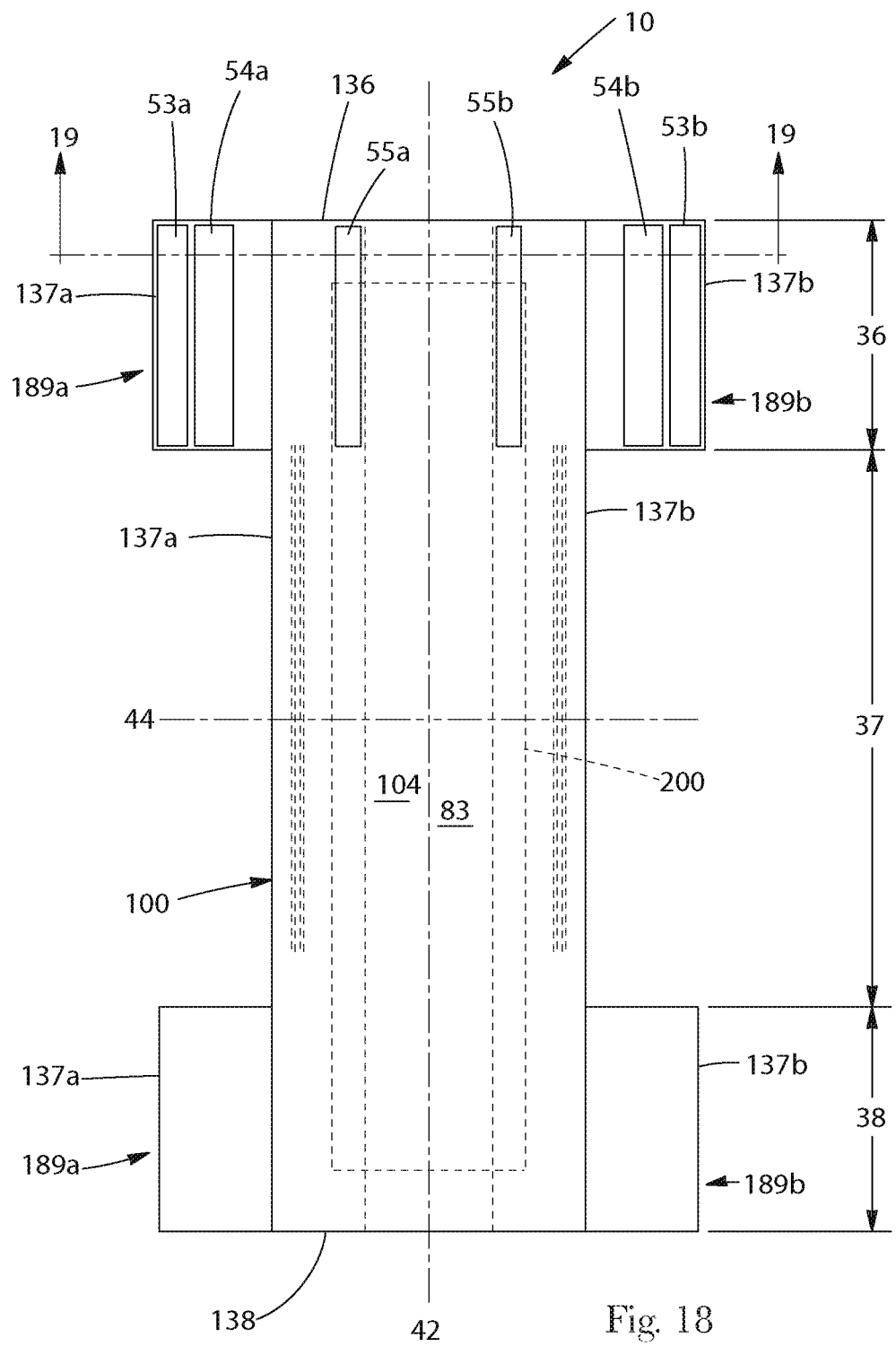

FIG. 18 is a plan view of a simplified absorbent article shown in its flat, uncontracted state prior to being formed into a pant in accordance with one non-limiting embodiment. In FIG. 18, the exterior surface of the absorbent article is shown facing the viewer.

Figure 19:
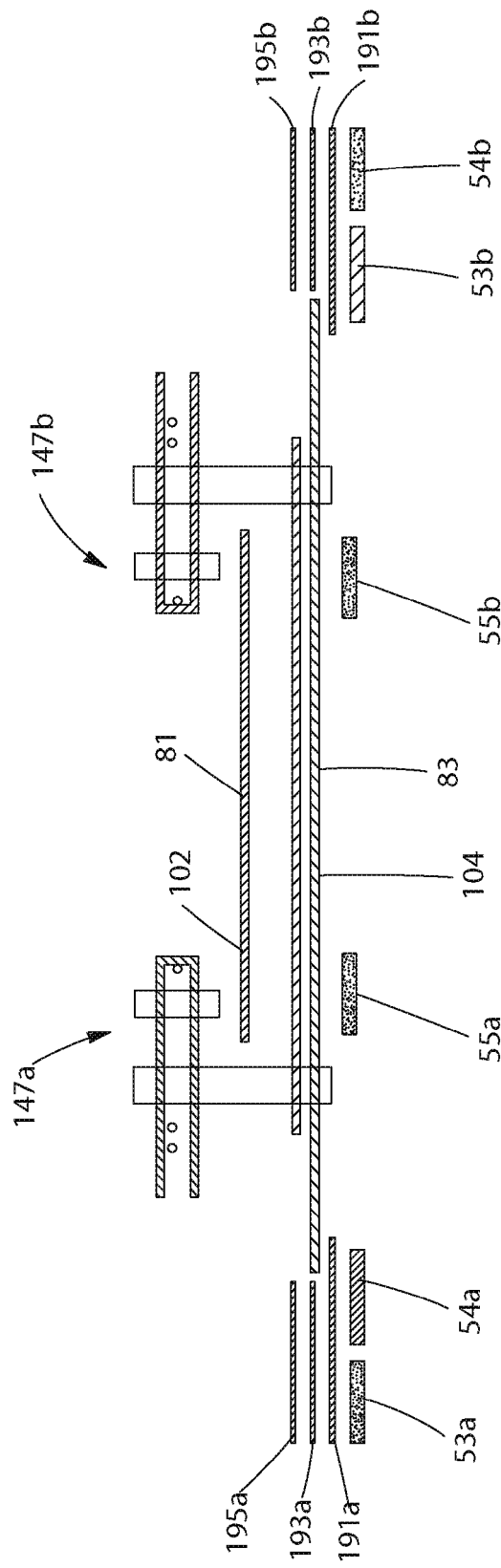

FIG. 19 is a cross-sectional view of the absorbent article of FIG. 18, taken along line A-A in accordance with one non-limiting embodiment.

Figure 20:
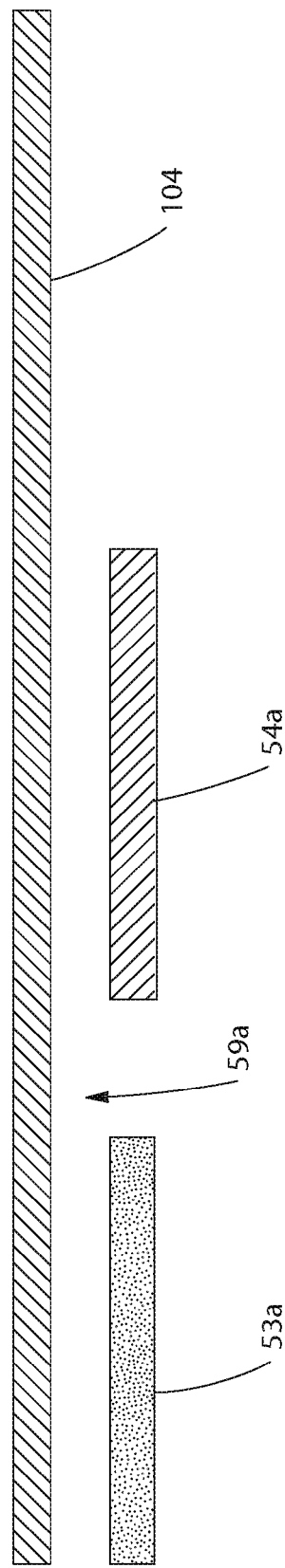

FIG. 20 is a cross-sectional view of the absorbent article of FIG. 1, taken along line B-B in accordance with one non-limiting embodiment.

Figure 21:
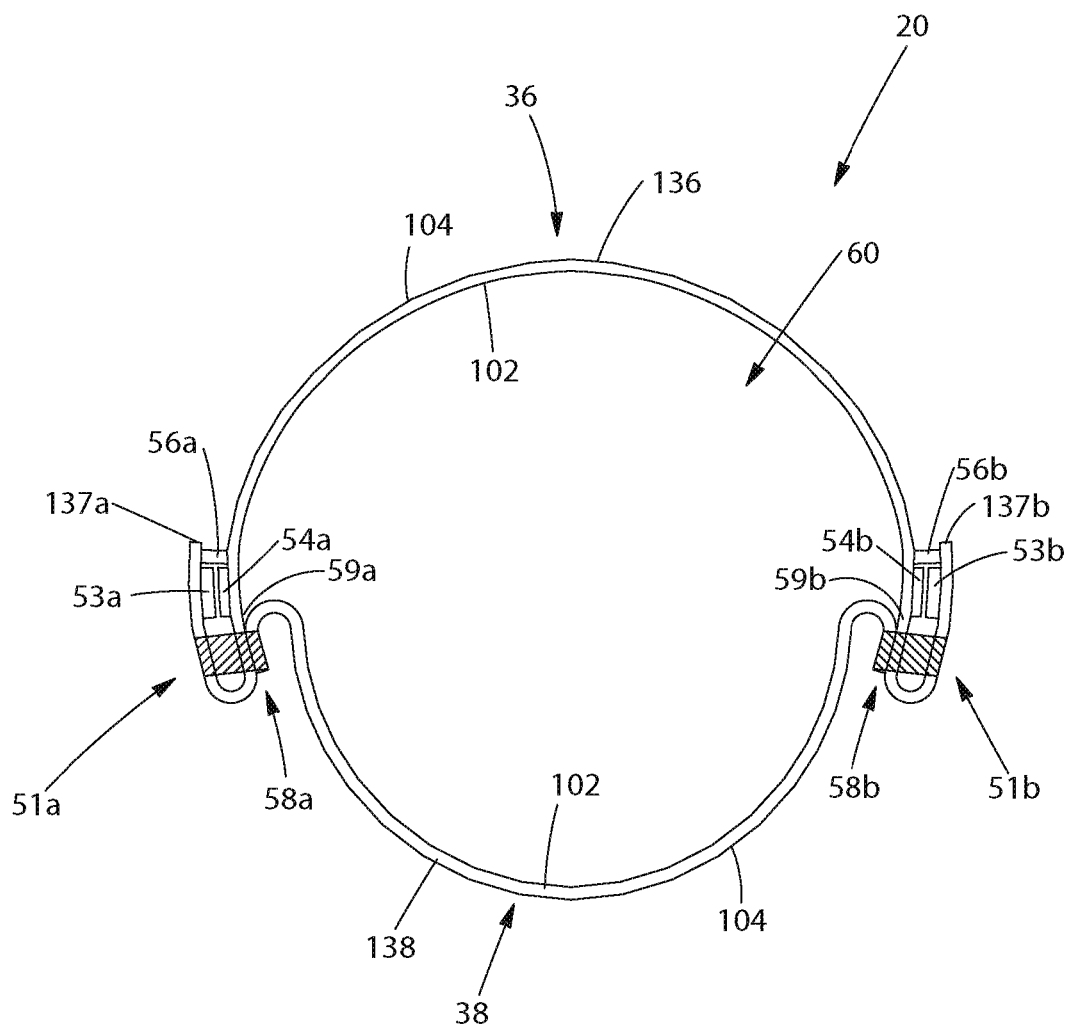

FIG. 21 is a top view of a pant formed with a flange seam in accordance with one non-limiting embodiment.

Figure 22:
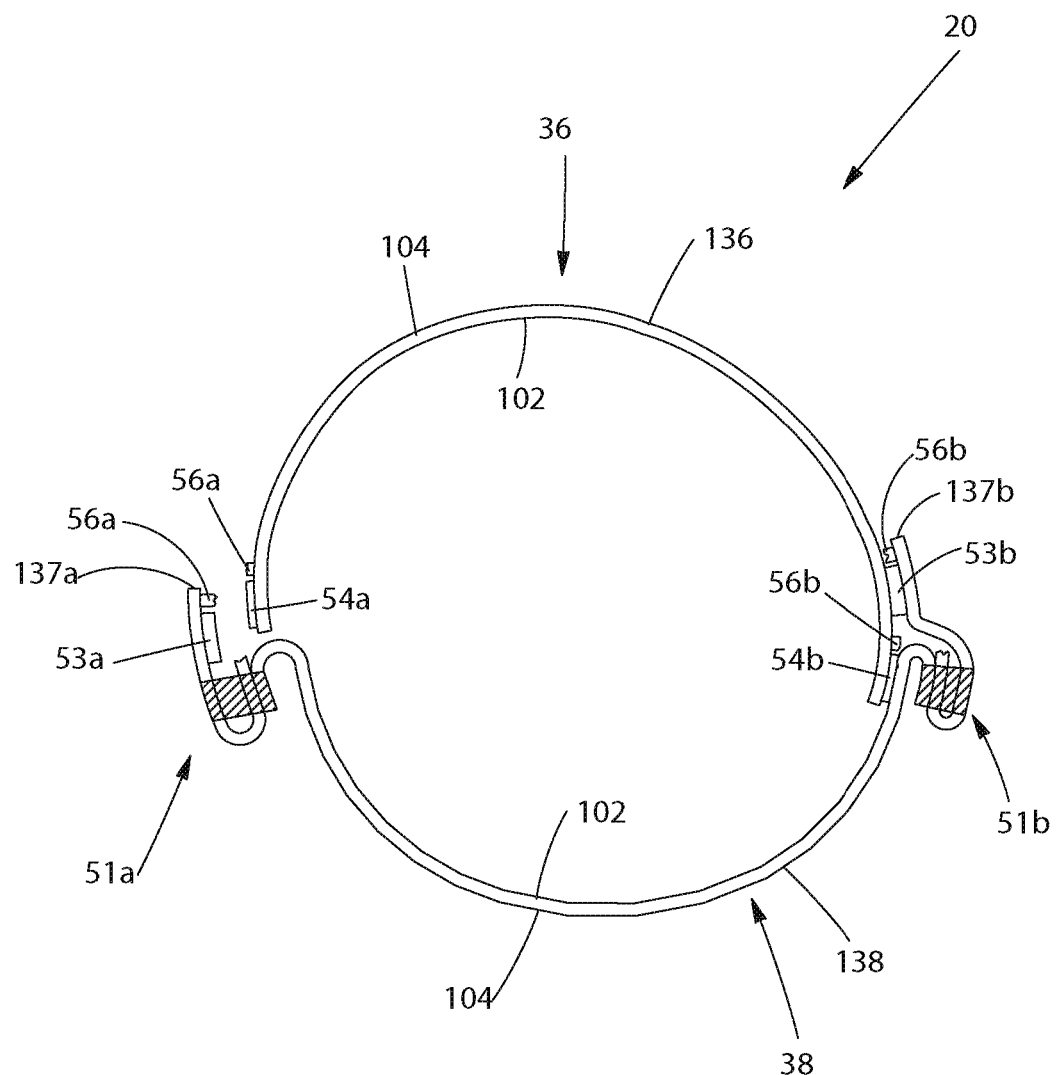

FIG. 22 is a top view of the pant of FIG. 21 with the separation zones separated and the closure bonds broken. A first side of the pant is unfastened, while the second side of the pant is refastened to a front waist region of the pant.

Figure 23:
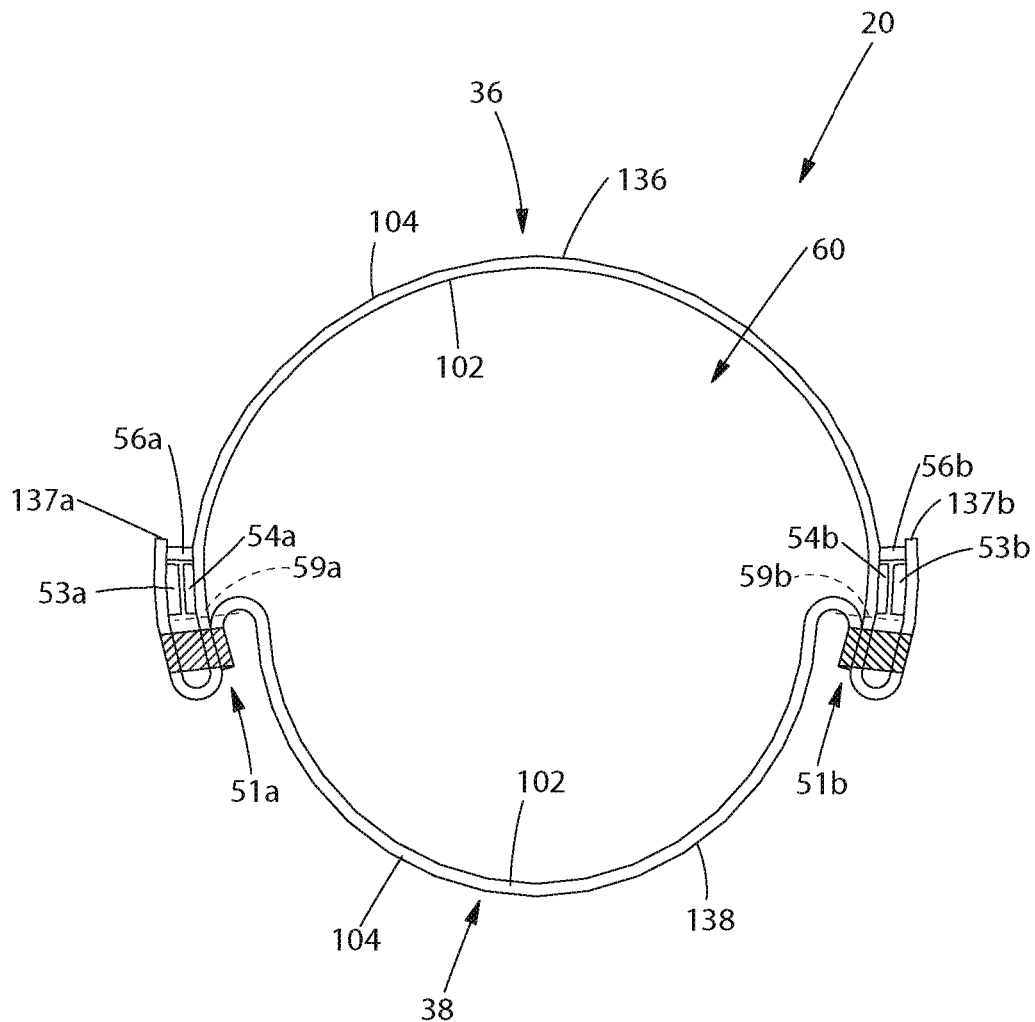

FIG. 23 is a top view of a pant formed with a flange seam in accordance with one non-limiting embodiment.

Figure 24:
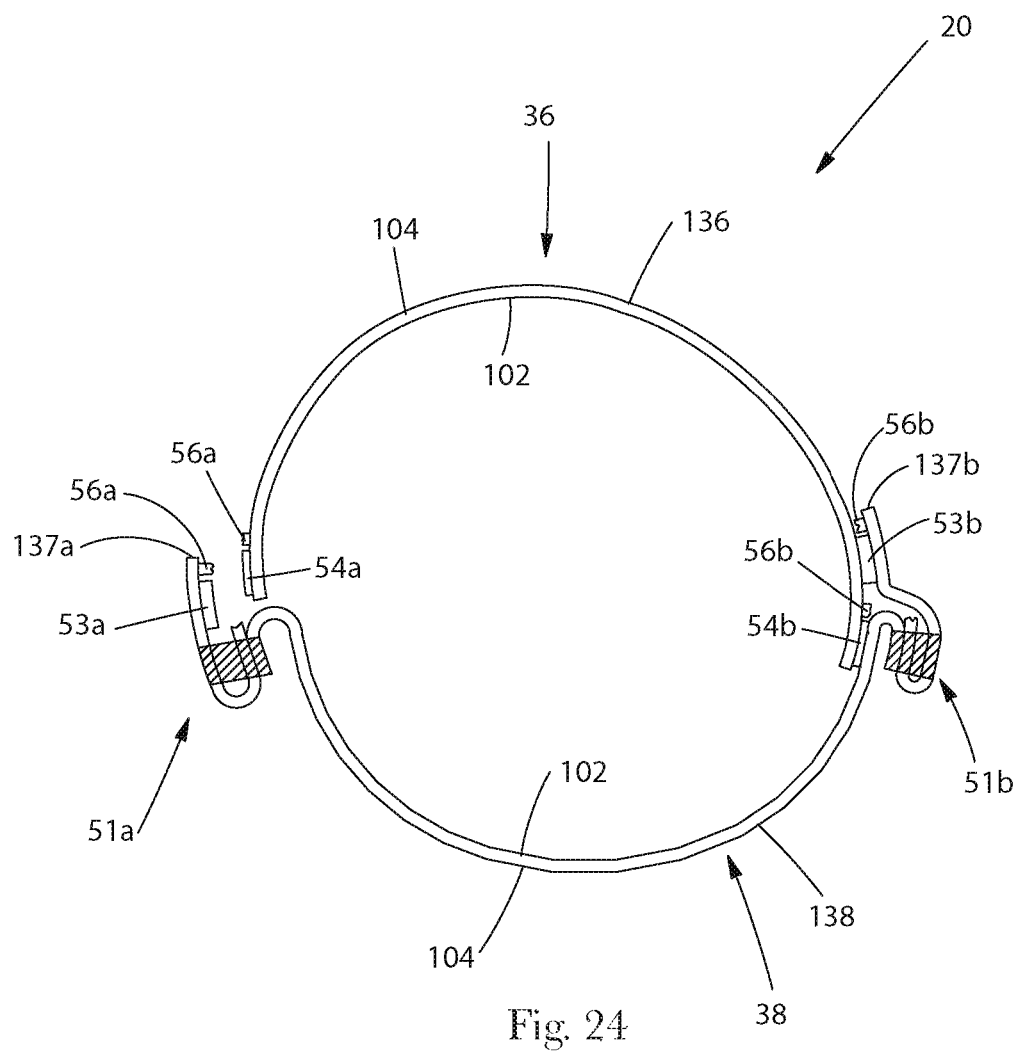

FIG. 24 is a top view of the pant of FIG. 23 with the separation zones separated and the closure bonds broken. A first side of the pant is unfastened, while the second side of the pant is refastened to a front waist region of the pant.

Figure 25:
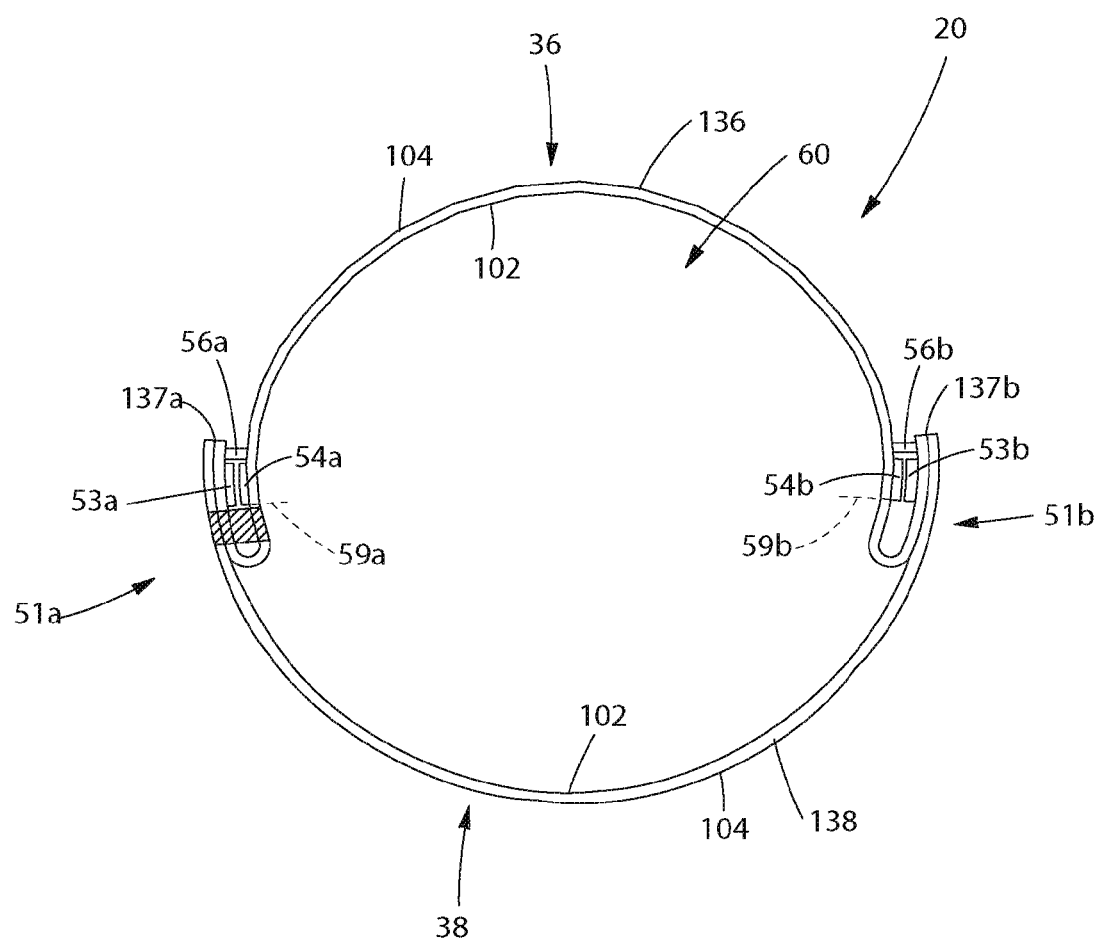

FIG. 25 is a top view of a pant formed with a flange seam in accordance with one non-limiting embodiment.

Figure 26:
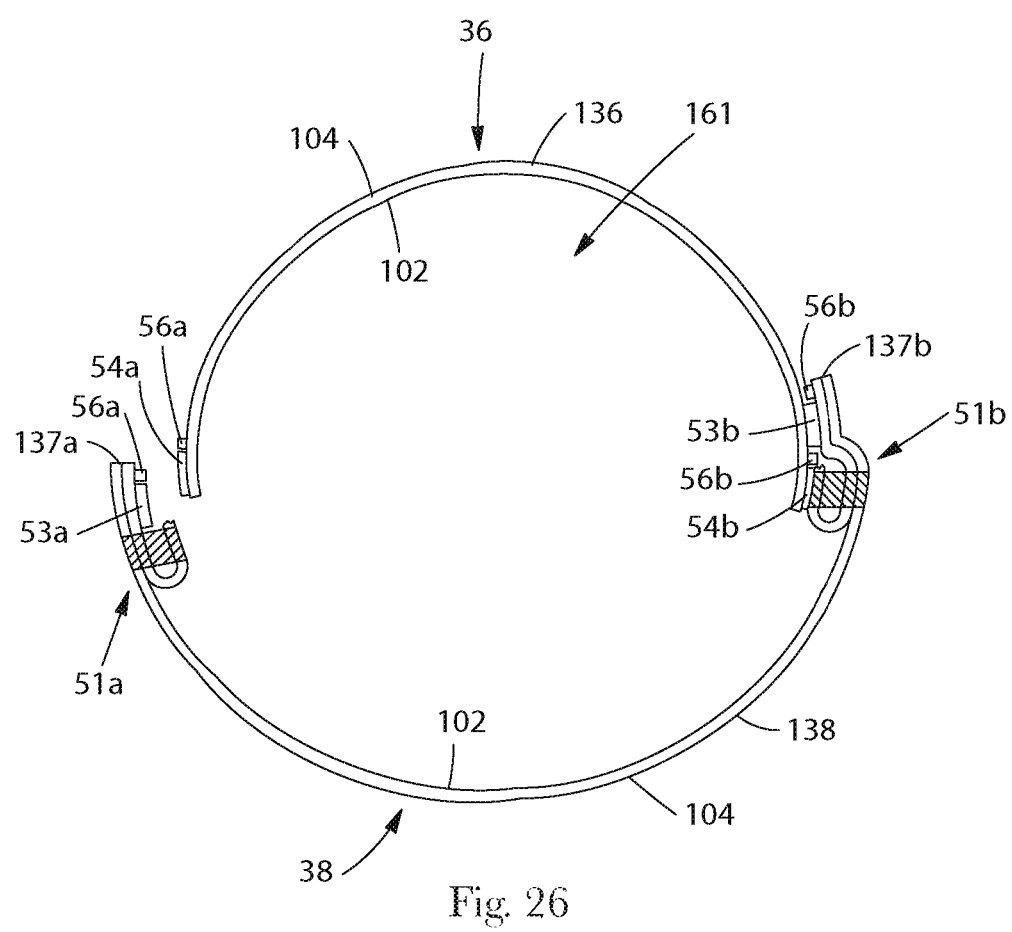

FIG. 26 is a top view of the pant of FIG. 25 with the separation zones separated and the closure bonds broken. A first side of the pant is unfastened, while the second side of the pant is refastened to a front waist region of the pant.

Figure 27:
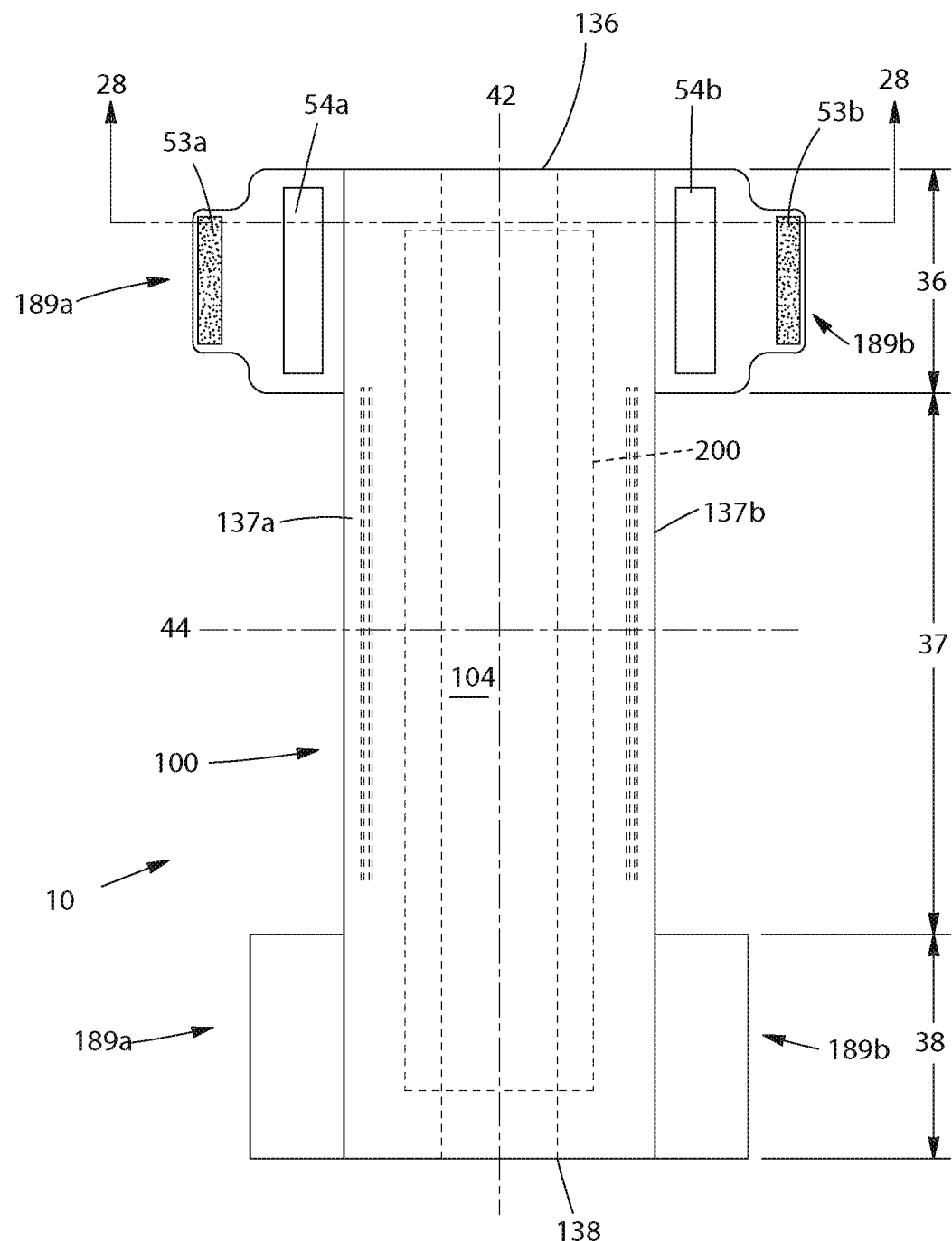
Figure 30A:
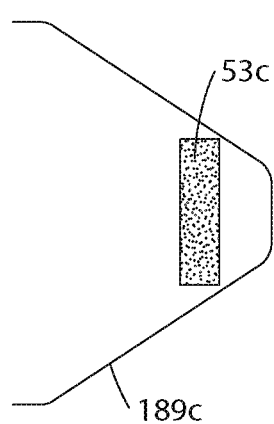
Figure 30B:
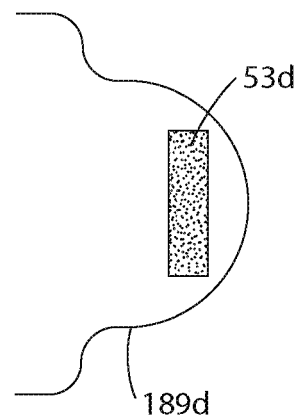
Figure 30C:
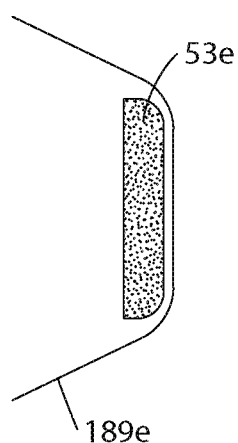
Figure 30D:
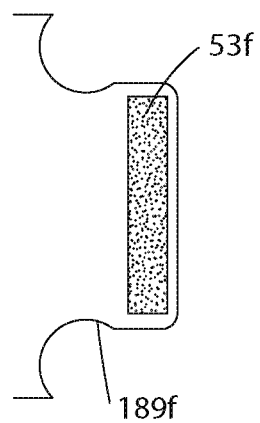
Figure 30E:
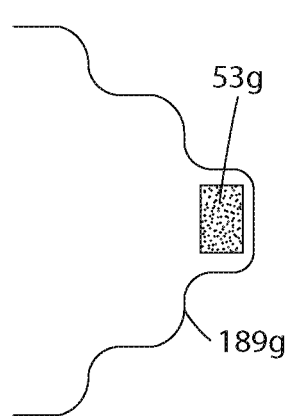
Figure 30F:
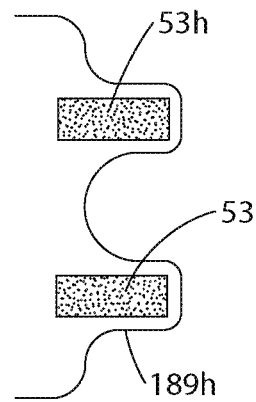
Figure 30G:
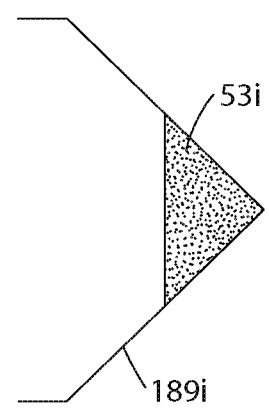
Figure 30H:
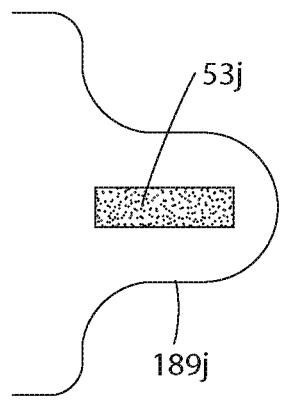

FIG. 27 is a plan view of a simplified absorbent article shown in its flat, uncontracted state prior to being formed into a pant in accordance with one non-limiting embodiment. In FIG. 27, the exterior surface of the absorbent article is shown facing the viewer.

FIG. 28 is a cross-sectional view of the absorbent article of FIG. 27, taken along line A-A in accordance with one non-limiting embodiment.

FIG. 29 is an alternative cross-sectional view of the absorbent article of FIG. 27, taken along line A-A in accordance with one non-limiting embodiment.

FIGS. 30A-H illustrate alternate side panel designs in accordance with various non-limiting embodiments.

FIG. 31 is a top view of a pant formed with a flange seam in accordance with one non-limiting embodiment.

Figure 32:
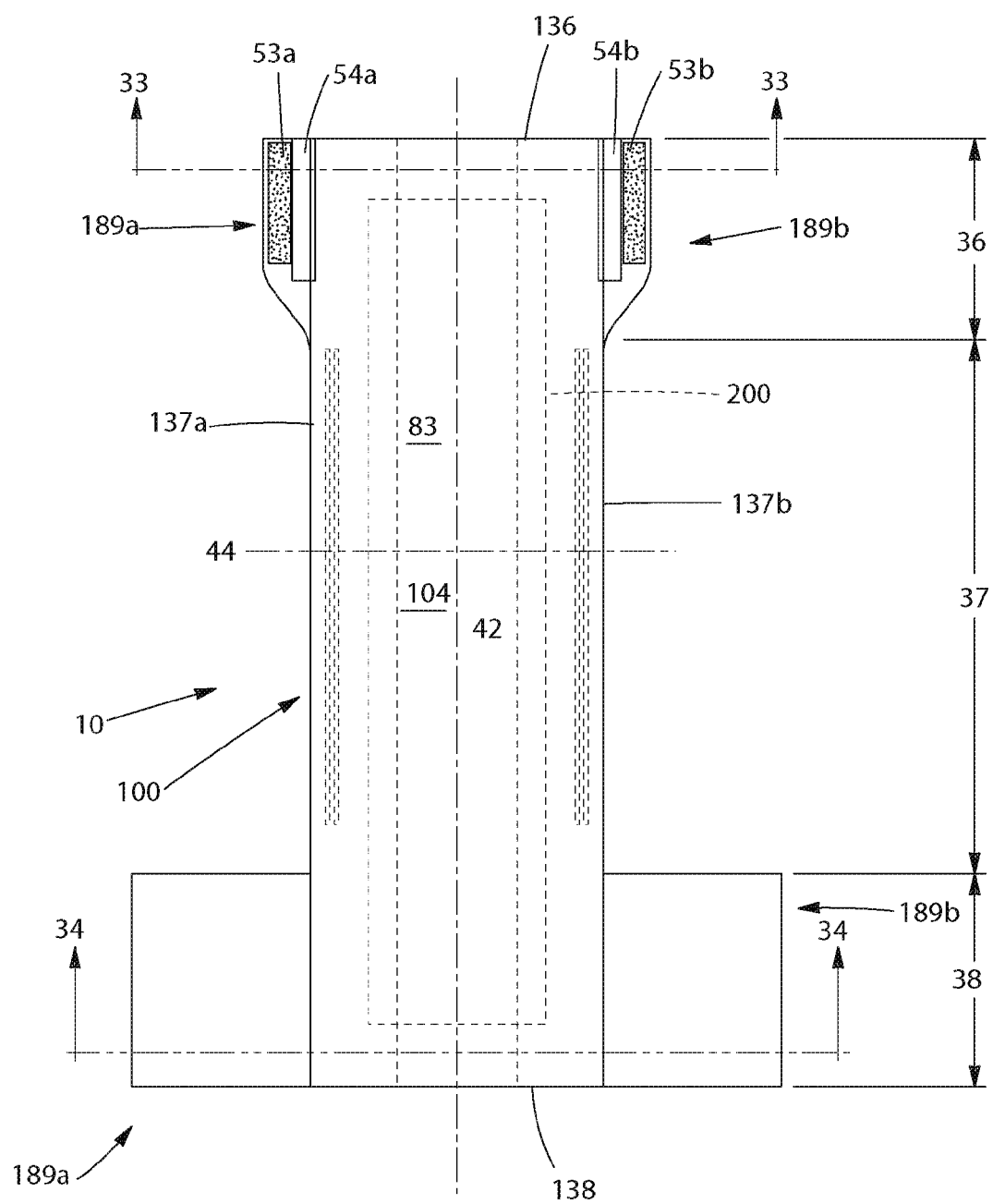

FIG. 32 is a plan view of a simplified absorbent article shown in its flat, uncontracted state prior to being formed into a pant in accordance with one non-limiting embodiment. In FIG. 32, the exterior surface of the absorbent article is shown facing the viewer.

FIG. 33 is a cross-sectional view of the absorbent article of FIG. 32, taken along line A-A in accordance with one non-limiting embodiment.

FIG. 34 is a cross-sectional view of the absorbent article of FIG. 32, taken along line B-B in accordance with one non-limiting embodiment.

Figure 35:
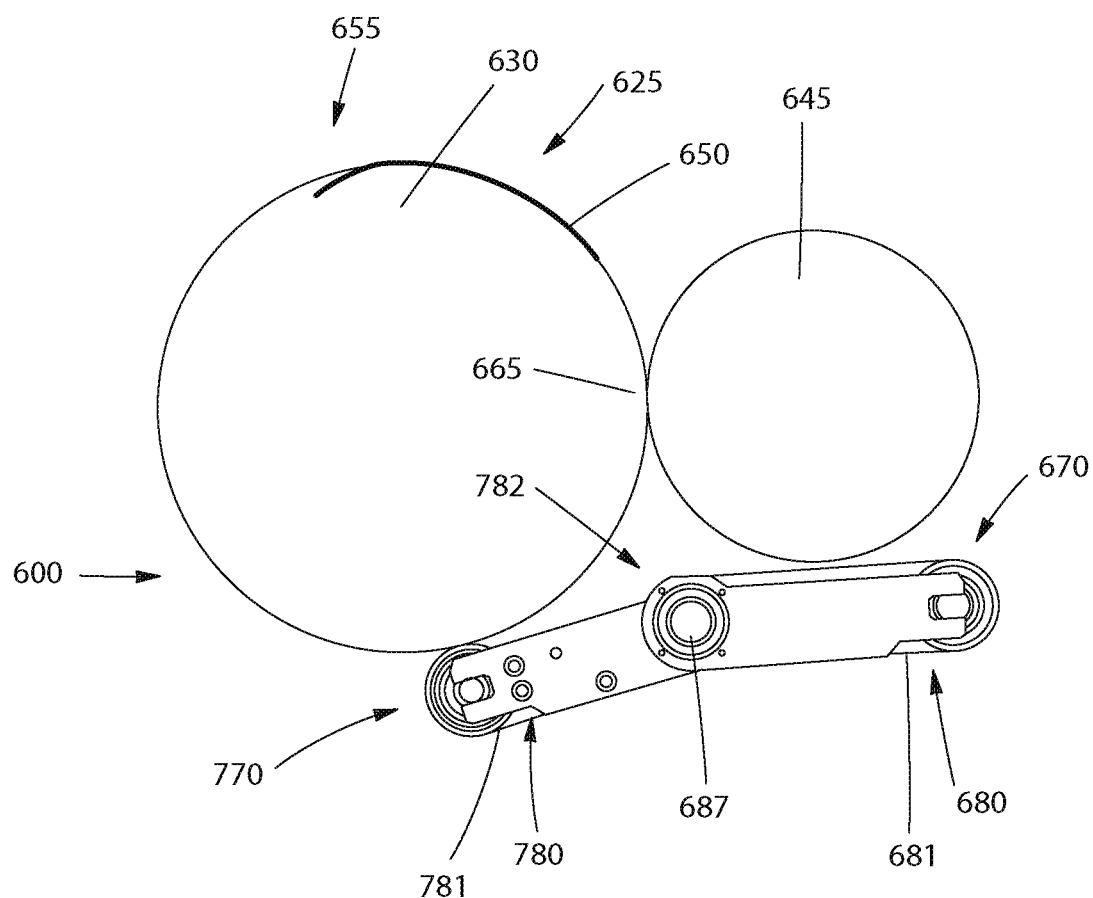

FIG. 35 illustrates equipment used to make the absorbent articles of the present disclosure in accordance with various non-limiting embodiments.

DETAILED DESCRIPTION

Various non-limiting embodiments of the present disclosure will now be described to provide an overall understanding of the principles of the structure, function, manufacture, and use of the apparatuses and methods disclosed herein. One or more examples of these non-limiting embodiments are illustrated in the accompanying drawings. Those of ordinary skill in the art will understand that the apparatuses and methods specifically described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

In this description, the following terms generally have the following meanings:

The term "absorbent article" refers to a device that is placed against or in proximity to a body of a wearer to absorb and contain the various exudates discharged from the body. Example absorbent articles may comprise diapers, training pants, pants, pull-on pant-type diapers (i.e., a diaper having a pre-formed waist opening and leg openings, such as illustrated in U.S. Pat. No. 6,120,487), refastenable diapers, incontinence briefs and undergarments, diaper holders and liners, feminine hygiene garments, and related articles.

The term "fastening component" refers to the fastening element or elements that define an area of refastenable attachment. The fastening components enable refastening of the absorbent article to reconfigure the waist and leg openings into a closed configuration until the fastening components are separated. A fastening component may comprise of one or more refastenable fastening elements, e.g., hooks, loops, bulbs, mushrooms, arrowheads, balls on stems, buttons, snaps, refastenable cohesives, selective refastenable adhesives, etc. A fastening component may be opened and subsequently re-closed, reliably, without destroying the fastening component. A fastening component comprises those elements of a fastening system that form the area of attachment via direct surface-to-surface contact forming a refastenable closure. For the purpose of clarity, surface-to-surface contact encompasses contact between a surface of a hook material and a surface of a loop material, for example. For instance, a tab member joined to a backsheet would not be a fastening member as discussed. The fastening component may be the hooks or the loops that are joined to the tab and connect with the other fastening components or a portion of an absorbent article.

The term "initial waist opening circumference" refers to the circumference of a waist opening of the disposable training pant at the time the disposable training pant is placed in the package and, subsequently, when it is removed from the package by the consumer.

The term "lateral" refers to a direction running from a side edge to an opposing side edge of the absorbent article and generally at a right angle to the longitudinal direction. Directions within ±45° of the lateral direction are considered to be "lateral".

The term "longitudinal" refers to a direction running from a waist edge to an opposing waist edge of the absorbent article and generally parallel to the maximum linear dimension of the article. Directions within ±45° of the longitudinal direction are considered to be "longitudinal".

The term "pant" (also referred to as "disposable training pant," "training pant," and "pull-on pant-type diaper") refers to disposable absorbent articles having a continuous perimeter waist opening and continuous perimeter leg openings designed for infant, child, or adult wearers (hereafter "wearer"). A pant may be configured with a continuous or closed waist opening and at least one continuous or closed leg opening prior to the pant being applied to the wearer. A pant may be pre-formed by any suitable technique including, but not limited to, joining together portions of the absorbent article using any refastenable and/or permanent closure member(s) (e.g., seams, heat bonds, pressure welds, adhesives, cohesive bonds, mechanical fasteners, etc.). A pant may be preformed anywhere along its circumference in the waist region (e.g., side fastened, front waist fastened, rear waist fastened). Example pants and pant configurations are disclosed in U.S. Pat. Nos. 5,246,433, 5,569,234, 6,120,487, 6,120,489, 4,940,464, 5,092,861, 5,897,545, 5,957,908, and U.S. Pat. Publ. No. 2003/0233082.

The term "secondary waist opening circumference" refers to the circumference of the waist opening of the pant after the initial waist opening circumference has been broken and the pant has been refastened.

The term "side edge seam" refers to a given side edge wherein a portion of the side edge, or region adjacent the side edge, in the front waist region is joined to a portion of the same side edge, or region adjacent the side edge, in the rear waist region to define closed, encircled leg openings and a closed waist opening. Because the side edge seam is closed with a permanent closure member, it cannot be opened without causing the permanent closure member to fail (i.e., the permanent closure member cannot again be reliably reclosed).

To improve the overall functionality of a refastenable side seam pant, it may be desirable to make the initial opening force and the opening force after refastening or re-closing the pant independent of each other. Stated another way, separate closure or fastening members may be used to create an initial waist opening circumference and a second waist opening circumference (refastened). Having fastening components initially disposed in a non-engaged orientation when the initial waist opening circumference is formed makes the initial opening force of the initial waist opening circumference independent of the opening force of the second waist opening circumference once the pant has been refastened or re-closed. If the fastening components are not initially engaged, the initial opening force may be controlled independently of the fastening components.

In one embodiment, the initial opening force may be a function of the strength of a separation zone defined in the pant. Since the initial opening force is independent of the subsequent opening force after refastening, a high subsequent opening force may be delivered thereby providing a more secure and stable side seam closure after refastening of the side seam. In addition, a pant that has permanent side seams as the structural elements that define the side seams, the waist opening, and the leg openings tend to deliver more robust and reliable side seams. In one embodiment, the permanent side seams may be formed using bonding, such as thermal bonding and/or ultrasonic bonding, for example, or may alternatively be formed using adhesives, permanent cohesives, or other suitable bonding or closure devices.

In one embodiment, both of the fastening components (i.e., first fastening component and second fastening component) of each side seam may be disposed or formed within the front waist region of a pant to improve access to the fastening components. It is noted that the second fastening component may merely be disposed on or form a portion of the front waist region, to which the first fastening component is disposed. Improving access to the fastening components by placing the first and second fasting components in the front waist region may make opening and refastening of the pant significantly easier for a caregiver and allow front waist region to front waist region fastening, making the pant changing or pant checking process easier for the caregiver when the wearer is standing in front of the caregiver (e.g., face-to-face) or when the wearer is laying on his or her back. In addition, fastening of the fastening components in the front waist region of a pant or diaper is also familiar to caregiver since this is similar to tape-style diapers.

In one embodiment, both of the fastening components may also be disposed on the same surface of the pant. In one embodiment, the fastening components may both be disposed on or formed with an exterior surface or a garment-facing surface of the pant thereby making both of the fastening components readily recognizable for the caregiver, thereby making a pant change or pant check faster and easier for the caregiver.

These pull-on training pants have proven to be particularly desirable and useful products for wearers, such as children in the potty training stage, for example. Such pants generally comprise an absorbent chassis comprising a liquid impervious backsheet, a liquid pervious topsheet, and an absorbent core positioned intermediate the topsheet and the backsheet. The absorbent chassis and the side panels (when present) may be pre-closed to form an initial waist opening circumference and two initial leg opening circumferences.

Some pants have permanent side seams, or seams that cannot be refastened once broken, forming the leg opening circumferences and the waist opening circumference. Such permanent seams are generally pre-closed to provide a pant that looks like underwear and may be applied like underwear (i.e., slid up the legs of a wearer and into position around the wearer's waist region). Pants with permanent side seams, however, may require a separate element for disposal of the pants, such as a disposal tape positioned on the external surface of the pants (such that the pant can be wrapped up and disposed of). Other pants have non-permanent side seams and are refastenable thereby allowing a caregiver to open and close the waist and leg openings of the pants similar to a traditional tape-style diaper.

The ability to open and refasten the pants offers convenience to the caregiver. For instance, it might be more convenient to apply the pants as a traditional tape-style diaper when away from home or when it is inconvenient to remove the clothing and/or shoes of the wearer. Because it is difficult to predict when the wearer will need to be changed and, therefore, when a particular mode of application will be needed, it would be beneficial to provide a pant that is adaptable to being applied either as a traditional tape-style diaper or as a disposable training pant. In addition, a product that may be applied like a traditional tape-style diaper or a disposable training pant also permits inspection of the interior of the product without having to slide the product down the legs of the wearer. The pants of the present disclosure provide dual functionality with regard to application and removal while enabling the easy wrapping up and disposal of the used pants.

Further to the above, some related art pants may be easier for a wearer to remove than the pant of the present disclosure. In related art pants, the overlap of the two portions that refasten the pants about the side seams often creates a flap that the wearer may grasp and pull to remove the pants at an undersirable time. Because this flap generally runs from the waist region to the leg openings, its length allows the wearer to easily remove the pant regardless of the wearer's dexterity. And, because the closure of the flap creates the initial waist opening circumference of the training pant, once opened, the pant may fall off of the wearer.

To alleviate some of the problems of the related art pants, the present disclosure, in part, teaches a pant that minimizes the opportunity given to a wearer to remove the pant while still offering refastenable convenience to the caregiver. The pant of the present disclosure comprises an opening and re-closure system that require greater dexterity to open owing at least to the location of the opening and closure system on the pant. In one embodiment, the pant may comprise one or more permanent side seams which form the absorbent article into the pant with pre-closed waist and leg openings and fastening components that enable ease of re-closing and/or disposal of the pant. In one embodiment, the opening and re-closure system may be oriented so that the closure member is unapparent to the wearer. Further, if the wearer does open the fastening components of the refastenable closure system, the pant will not fall off since the fastening components do not, in their initial non-engaged position, form the initial waist opening circumference and leg opening circumferences. As a result, the pant of the present disclosure allows the caregiver to decide in what manner the pant will be applied to the wearer (as a pant or as a traditional tape-style diaper). Further, the caregiver receives the added security that the pant may not be easily removed by the wearer. Therefore, creating a pant with the flexibility to apply as a traditional tape-style diaper or a pant and with the aesthetics and appearance of underwear provides the best overall experience for the wearer and the caregiver.

The various components used to form various example pants of the present disclosure will now be described in greater detail.

Absorbent Article

In one embodiment, an absorbent article may comprise an absorbent chassis comprising a topsheet, a backsheet, and an absorbent core disposed at least partially between the topsheet and the backsheet. The chassis may comprise a waistband, leg cuffs and/or elastic strands. In various embodiments, referring to FIGS. 1 and 2, an example absorbent article 10 is shown in its flat uncontracted state prior to being formed into a pant. The absorbent article 10 may be formed into a pant 20 shown in FIGS. 3 and 8, for example. Various suitable configurations of pant 20 are disclosed in U.S. Pat. Nos. 5,246,433, 5,569,234, 6,120,487, 6,120,489, 4,940, 464, 5,092,861, 5,897,545, 5,957,908, and U.S. Pat. Publ. Nos. 2003/0233082, 2003/0088220, 2003/0233082, 2005/0215971, 2005/0215970, 2007/0078427, 2007/0093769, 2007/0074381, 2007/0078426, 2007/0078427, 2007/0093769, and 2008/0107861.

In one embodiment, referring to FIGS. 1 and 2, one end portion of the absorbent article 10 may be configured as a front waist region 36 and the longitudinally opposing end portion may be configured as a back waist region 38. An intermediate portion of the absorbent article 10 extending longitudinally between the front waist region 36 and the back waist region 38 may be configured as a crotch region 37. In one embodiment, although not illustrated as such, the length of each of the front waist region 36, the back waist region 38 and the crotch region 37 may be about ⅓ of the length of the absorbent article 10, for example. In other embodiments, the length of each of the front waist region 36, the back waist region 38 and the crotch region 37 may have other dimensions, for example. In various embodiments, the absorbent article 10 may have a laterally extending front waist end edge 136 in the front waist region 36 and a longitudinally opposing and laterally extending back waist end edge 138 in the back waist region 38.

In one embodiment, still referring to FIGS. 1 and 2, a chassis 100 of the absorbent article 10 may comprise a first longitudinally extending side edge 137a and a laterally opposing and second longitudinally extending side edge 137b. Both of the side edges 137 may extend longitudinally between the front waist end edge 136 and the back waist end edge 138. The chassis 100 may form a portion of the laterally extending front waist end edge 136 in the front waist region 36 and a portion of the longitudinally opposing and laterally extending back waist end edge 138 in the back waist region 38. Furthermore, the chassis 100 may comprise an interior surface 102, an exterior surface 104, a longitudinal axis 42, and a lateral axis 44. The longitudinal axis 42 may extend through a midpoint of the front waist end edge 136 and through a midpoint of the back waist end edge 138, while the lateral axis 44 may extend through a midpoint of the first side edge 137a and through a midpoint of the second side edge 137b.

In various embodiments, a portion of or the whole absorbent article 10 may be made to be laterally extensible. The extensibility of the absorbent article 10 may be desirable in order to allow the absorbent article 10 to conform to a body of a wearer during movement by the wearer. The extensibility may also be desirable, for example, in order to allow the caregiver to extend the front waist region 36, the back waist region 38, the crotch region 37, and/or the chassis 100 to provide additional body coverage for wearers of differing size, i.e., to tailor the absorbent article 10 to the individual wearer. Such extension may provide the absorbent article 10 with a generally hourglass shape, so long as the crotch region 37 is extended to a relatively lesser degree than the waist regions 36 and/or 38. This extension may also impart a tailored appearance to the absorbent article 10 during use.

Topsheet

In one embodiment, again referring to FIGS. 1 and 2, the absorbent article 10 may comprise a topsheet 81. The topsheet 81 may be compliant, soft feeling, and non-irritating to the wearer's skin and may be elastically stretchable in one or more directions. Further, the topsheet 81 may be liquid pervious, permitting liquids (e.g., menses, urine, and/or runny feces) to penetrate through its thickness. Various topsheets may also comprise a hydrophilic material, for example, which is configured to draw bodily fluids into an absorbent core of the chassis 100 when these fluids are expelled from the body. A suitable topsheet 81 may be manufactured from a wide range of materials, such as woven and nonwoven materials, apertured or hydroformed thermoplastic films, apertured nonwovens, porous foams, reticulated foams, reticulated thermoplastic films, and/or thermoplastic scrims, for example. Suitable apertured films may comprise those described in U.S. Pat. Nos. 5,628,097, 5,916, 661, 6,545,197, and 6,107,539. Apertured film topsheets typically may be pervious to bodily exudates, yet non-absorbent, and have a reduced tendency to allow fluids to pass back through and rewet the wearer's skin. Suitable woven and nonwoven materials may comprise natural fibers, such as, for example, wood or cotton fibers, synthetic fibers, such as, for example, polyester, polypropylene, or polyethylene fibers, or combinations thereof. If the topsheet 81 comprises fibers, the fibers may be spunbond, carded, wet-laid, meltblown, hydroentangled, or otherwise processed, for example, as is generally known in the art.

Backsheet

In one embodiment, referring to FIGS. 3 and 8, for example, the absorbent article 10 may comprise a backsheet 83. In FIGS. 3 and 8, the absorbent article 10 is shown formed into a pant 20. The backsheet 83 may be impervious, or at least partially impervious, to fluids or body exudates (e.g., menses, urine, and/or runny feces) and may be manufactured from a thin plastic film, although other flexible liquid impervious materials may also be used. The backsheet 83 may prevent the body exudates or fluids absorbed and contained in an absorbent core of the absorbent article 10 from wetting articles which contact the absorbent article 10, such as bedsheets, pajamas, clothes, and/or undergarments, for example, when formed into the pant 20. The backsheet 83 may comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). A suitable backsheet may comprise a polyethylene film having a thickness of from about 0.012 mm (0.5 mils) to about 0.051 mm (2.0 mils). Examples of polyethylene films are manufactured by Clopay Corporation of Cincinnati, Ohio, under the designation BR-120 and BR-121, and by Tredegar Film Products of Terre Haute, Ind., under the designation XP-39385. In one embodiment, the backsheet 83 may be embossed and/or matte-finished to provide a more cloth-like appearance. Further, the backsheet 83 may permit vapors to escape from the absorbent core of the absorbent article 10 (i.e., the backsheet 83 is breathable) while still preventing, or at least inhibiting, fluids or body exudates from passing through the backsheet 83. In one embodiment, the size of the backsheet 83 may be dictated by the size of the absorbent article 10 and the design or configuration of the pant 20 to be formed, for example.

Absorbent Core

In various embodiments, referring to FIG. 1, the absorbent article 10 may comprise an absorbent core 200 that is disposed between the topsheet 81 and the backsheet 83. The absorbent core 200 may comprise a laterally extending front edge 236 in the front waist region 36, a longitudinally opposing and laterally extending back edge 238 in the back waist region 38, a first longitudinally extending side edge 237a, and a laterally opposing and second longitudinally extending side edge 237b. Both of the side edges 237 may extend longitudinally between the front edge 236 and the back edge 238. In one embodiment, more than one absorbent core 200 or more than one absorbent core layer may be provided in an absorbent article 10, for example. The absorbent core 200 may be any suitable size or shape that is compatible with the absorbent article 10. Example absorbent structures for use as the absorbent core 200 of the present disclosure that have achieved acceptance and commercial success are described in U.S. Pat. Nos. 4,610,678, 4,673, 402, 4,888,231, and 4,834,735.

In one embodiment, suitable absorbent cores may comprise cellulosic airfelt material. For instance, such absorbent cores may comprise less than about 40%, 30%, 20%, 10%, 5%, or even 1% of the cellulosic airfelt material as determined by weight. Additionally, such an absorbent core may be primarily comprised of an absorbent gelling material in amounts of at least about 60%, 70%, 80%, 85%, 90%, 95%, or even about 100% as determined by weight. Furthermore, a portion of the absorbent core may comprise a microfiber glue (if applicable). Such absorbent cores, microfiber glues, and absorbent gelling materials are described in U.S. Pat. Nos. 5,599,335, 5,562,646, 5,669,894, 6,790,798, and 7,521,587 and in U.S. Pat. Publ. No. 2004/0158212.

Leg Cuffs

In one embodiment, referring to FIGS. 1 and 2, the chassis 100 of the absorbent article 10 may comprise longitudinally extending and laterally opposing leg cuffs 147a and 147b that are disposed on the interior surface of the chassis 100 that faces inwardly toward the wearer and contacts the wearer. The leg cuffs 147 may comprise one or more elastic gathering members 159 disposed at or adjacent the proximal edge of one or both of the leg cuffs 147. In addition to the elastic gathering members 159, the leg cuff may comprise one or more elastic strands 168 disposed at or adjacent the distal edge 139 of one or both of the leg cuffs 147. The elasticized leg cuffs 147 may comprise several embodiments for reducing the leakage of body exudates or fluids in the leg regions. The elasticized leg cuffs 147 are sometimes referred to as leg bands, barrier cuffs, elastic cuffs, or gasketing cuffs.) Suitable elasticized leg cuffs 147 may comprise those described in U.S. Pat. Nos. 3,860,003, 4,909,803, 4,695,278, 4,795,454, 4,704,115, and 4,909,803, and U.S. Pat. Publ. No. 2009/0312730. The leg cuffs 147 may be formed by folding portions of the chassis 100 laterally inward, i.e., toward the longitudinal axis 42, to form both the respective leg cuffs 147 and the side edges 137 of the chassis 100. In other embodiments, the leg cuffs 147 may be formed by attaching an additional layer or layers to the chassis 100 at or adjacent to each of the respective side edges 137a and 137b of the chassis 100. In one embodiment, the chassis 100 may also comprise other elastics 141 disposed adjacent the side edges 137 which may cause the pant 20 to form into a "U" shape when allowed to relax thereby pulling the interior surface 102 of the front waist region 36 toward the interior surface 102 of the back waist region 38.

In one embodiment, again referring to FIGS. 1 and 2, each leg cuff 147 may comprise a proximal edge 157a and 157b. These edges 157a and 157b are positioned proximate to the longitudinal axis 42 compared to distal edges 139a and 139b. The leg cuffs 147 may overlap the absorbent core 200, i.e., the proximal edges 157a and 157b lie laterally inward of the respective side edges 237a and 237b of the absorbent core 200. Such an overlapped configuration may be desirable in order to impart a more finished appearance to the absorbent article 10 than that imparted by a non-overlapped configuration. In other embodiments, the leg cuffs 147 may not overlap the absorbent core 200.

In one embodiment, still referring to FIGS. 1 and 2, each leg cuff 147 may be attached to the interior surface 102 of the chassis 100 in a leg cuff attachment zone (not shown) adjacent to the front waist end edge 136 and in a longitudinally opposing leg cuff attachment zone (not shown) adjacent to the back waist end edge 138. In one embodiment, between the leg cuff attachment zones, the proximal edge 157 of the leg cuff 147 remains free, i.e., not attached to the interior surface 102 of the chassis 100 or to the absorbent core 200. Also, between the longitudinally opposing leg cuff attachment zones, each leg cuff 147 may comprise one or more (specifically including one, two, three, or four elastic strands per leg cuff 147) longitudinally extensible cuff elastic gathering members 159 that may be disposed at or adjacent to the proximal edge 157 of the leg cuff 147 by any suitable methods. Each of such cuff elastic gathering members 159 may be attached over the leg cuff's entire length or over only a portion of the leg cuff's length. For example, such cuff elastic gathering members 159 may be attached only at or near the leg cuff's longitudinally opposing ends and may be unattached at the middle of the leg cuff's length. Such cuff elastic gathering members 159 may be disposed in the crotch region 37 and may extend into one or both of the front waist region 36 and the back waist region 38. For example, in the exemplary chassis 100 shown in FIG. 2, an elastic gathering member 159 may be attached at or adjacent to the proximal edge 157 of each of the leg cuffs 147 and extends into both the front waist region 36 and the back waist region 38.

In various embodiments, each cuff elastic gathering member 159 may be enclosed inside a folded hem 170 for example. In various embodiments, the cuff elastic gathering members 159 may be sandwiched between two layers forming the leg cuff 147, by two layers of the chassis 100, or may be attached on a surface of the chassis 100 or the leg cuff 147 and remain exposed. In one embodiment, when stretched, the cuff elastic gathering member 159 disposed adjacent to each leg cuff's proximal edge 157 allows the leg cuff proximal edge 157 to extend to the flat uncontracted length of the chassis 100, e.g., the length of the chassis 100, as shown in FIG. 1. When allowed to relax, the cuff elastic gathering member 159 contracts to pull the front waist region 36 and the back waist region 38 toward each other and, thereby, bend the pant 20 into a "U" shape in which the interior of the "U" shape may be formed by the portions of the pant 20 that are intended to be placed toward the body of the wearer (i.e., interior surface 102). Because each of the proximal edges 157 remains free between the longitudinally oriented leg cuff attachment zones, the contractive force of the elastic gathering member 159 may lift the proximal edge 157 of the leg cuff 147 away from the interior surface 102 of the chassis 100. This lifting of the proximal edges 157 when the pant 20 is in the relaxed condition lifts the leg cuffs 147 into a position to serve as side barriers to prevent, or at least inhibit, leakage of bodily exudates.

In one embodiment, referring to FIG. 2, one or more (specifically including one, two, three, or four elastic strands per leg cuff 147) elastic strands 168a and 168b may be attached at or adjacent the side edges 137a and 137b of the chassis 100 or the distal edge 139 of the leg cuff 147. When allowed to relax, the elastic strands 168a and 168b may gather the side edges 137a and 137b of the chassis 100 and/or distal edges 139 of the leg cuff 147 to form side barriers and function as a second barrier to leakage of bodily exudates (e.g., urine and fecal waste).

In various embodiments, the leg cuff 147 may be formed into a cuff flap 631 and a side barrier 633. Particularly, a side barrier attachment zone 630 may be oriented between the elastic gathering member 159 and elastic strands 168. The placement of side barrier attachment zones 630a and 630b relative to the longitudinal axis 42 may have a direct and coupled effect on the depth of cuff flaps 631a and 631b and the size of the side barriers 633a and 633b. For example, as illustrated by FIG. 2, when the side barrier attachment zone 630 is moved laterally inward, the depth of the cuff flaps 631 may decrease and the size of the side barrier 633 may increase. Conversely, when the side barrier attachment zone 630 is moved laterally outward, the depth of the cuff flaps 631 may increase and the size of the side barriers 633 may decrease. The depth and/or size of the cuff flaps 631 and side barriers 633 may be adjusted for various applications to provide enhanced functionality. In one such embodiment, it has been found that reduced depth cuff flaps 631 and larger side barriers 633 provide better application ease with regard to a pull-on pant-style application. This configuration may increase the size of the leg opening enabling the wearer to step into the diaper 20 more easily. In another embodiment, it has been found that increasing the depth of the cuff flaps 631 and reducing the size of the side barriers 633 may provide improved leakage protection and increased perception of capacity.

For embodiments wherein the leg cuffs 147 are formed by attaching additional layers to the chassis 100 at or adjacent to each of the respective side edges 137a and 137b of the chassis 100, the one or more elastic strands 168a and 168b may be oriented and attached between the layers (e.g., layers forming the backsheet 83 and leg cuff 147).

Waistband

In one embodiment, referring to FIGS. 3 and 8, the pant 20 formed from the absorbent article 10 may comprise an elasticized waistband 82.

In one embodiment, the elasticized waistband 82 may provide improved fit and containment and may be configured to elastically expand and contract laterally to dynamically fit a wearer's waist. The elasticized waistband 82 may extend longitudinally inwardly from the waist edge of the pant 20 toward the waist edge of the absorbent core 200. In one embodiment, the pant 20 may have two elasticized waistbands 82, one positioned in the back waist region 38 and one positioned in the front wait region 36, although other pant embodiments may be constructed with a single elasticized waistband 82. The elasticized waistband 82 may be constructed in a number of different configurations including those described in U.S. Pat. Nos. 4,515,595 and 5,151,092.

In one embodiment, the elasticized waistbands 82 may comprise materials that have been "prestrained" or "mechanically prestrained" (i.e., subjected to some degree of localized pattern mechanical stretching to permanently elongate the material). The materials may be prestrained using suitable deep embossing techniques. In other embodiments, the materials may be prestrained by directing the material through an incremental mechanical stretching system as described in U.S. Pat. No. 5,330,458. The materials may then be allowed to return to their substantially untensioned condition, thus forming a zero strain stretch material that is extensible, at least up to the point of initial stretching. Examples of zero strain materials are disclosed in U.S. Pat. Nos. 2,075,189, 3,025,199, 4,107,364, 4,209,563, 4,834, 741, and 5,151,092.

Side Panels

In one embodiment, referring to FIGS. 1 and 2, the absorbent article 10 may comprise side panels 189 attached at or adjacent the side edges 137 of the chassis 100 in one or both of the front waist region 36 and/or the back waist region 38. In various embodiments, each side panel 189 may either be a discrete separate element affixed to the chassis 100 or may comprise a unitary piece of material that is neither divided nor discontinuous with an element of the chassis 100, for example, a backsheet, a topsheet, or a leg cuff. In various embodiments, a pair of laterally opposed side panels 189 may be attached adjacent the laterally opposing side edges 137a and 137b of the chassis 100 in the front waist region 36 and a longitudinally opposing pair of side panels 189 may be attached at or adjacent the laterally opposing side edges 137a and 137b of the chassis 100 in the back waist region 38. The side panels 189 in the front waist region 36 may have the same lateral extent from the side edge 137 of the chassis 100 to the distal edge 137a and 137b of each side panel 189 as the longitudinally opposed side panels 189 in the back waist region 38 or, alternatively, the side panels 189 disposed in the front waist region 36 may have different lateral extents as measured from the side edges 137 of the chassis 100 to the distal edge (also indicated as 137a and 137b) of the side panel 189 than the side panels 189 disposed in the back waist region 38. When side panels 189 are present, the distal edges 137 of the side panels 189 form a portion of the side edges 137 or the absorbent article 10. In various embodiments, the side panels 189 may comprise a first nonwoven material layer 191, an elastomeric film layer 193, and a second nonwoven material layer 195. The film layer 193 may be disposed intermediate, or at least partially intermediate, the first nonwoven material layer 191 and the second nonwoven material layer 195.

In one embodiment, the side panels 189 may be substantially rectangular in shape or may be shaped in such a way as to provide an integral tab for ease of opening and refastening to create the secondary waist opening circumference 61. The side panels 189 may be extensible or elastically extensible in the lateral direction and/or the longitudinal direction, for example. In various embodiments, the side panels 189 may comprise an elastomeric film, such as a nonwoven, or a combination of film and nonwoven. In one embodiment, the side panels 189 may also comprise a plurality of strand-like filaments and a nonwoven material, for example. The strand-like filaments may be elastically extensible in at least the lateral direction, for example. Suitable elastomeric side panels and absorbent articles comprising such side panels are disclosed in U.S. Pat. Nos. 5,669,897, 5,899,895, 4,940,464, 5,246,433, 5,545,158, 5,591,155, 5,897,545.

Side Edge Seam

In one embodiment, referring to FIGS. 3 and 8, the front waist region 36 and the back waist region 38 of the absorbent article 10 may be joined together to form the pant 20 having an initial waist opening circumference 60 and two leg openings circumferences 62. The joining of the front waist region 36 with the back waist region 38 may comprise side edge seams 51a and 51b. Such side edge seams 51 may be formed where the front and back waist regions 36 and 38 are joined such that the interior surface 102 of the front waist region 36 faces the interior surface 102 of the back waist region 38 in a face-to-face relationship, e.g., in a so-called flange seam attachment. Such side edge seams 51 are shown in FIGS. 3 and 8, for example.

The laterally opposing side edge seams 51 may extend laterally outward from the initial waist opening circumference 60 such that they each form a flange-style permanent side edge seam 51 that may be folded laterally inward toward either the front waist region 36 and/or back waist region 38 of the pant 20. Both of the side edge seams 51 may be pre-closed, meaning that the side edge seams 51 are closed prior to removal of the pant 20 from its package and, therefore, prior to being donned on the wearer. The initial waist opening circumference 60 and the leg opening circumferences 62 may be opened at predetermined separation zones 59, as described in further detail herein. In one embodiment, once broken, the side edge seams 51 may not be able to be re-closed to form a secondary waist opening circumference and secondary leg opening circumferences without the use of the first fastening components 53.

In one embodiment, the bonds of the side edge seams 51 may comprise permanent suitable bonds that are appropriate for the specific materials employed in construction of the pant 20. Suitable bond types may comprise discrete bonds, such as sonic sealed bonds, heat sealed bonds, high pressure bonds, radio frequency bonds, adhesive or cohesive bonds, sewed bonds, autogeneous bonds, and combinations thereof, for example. In various embodiments, the permanent side edge seams 51 may be joined by a predetermined pattern of heat/pressure or ultrasonic welds that are able to withstand the forces and stresses exacted onto the side edge seams 51 during application and wear of the pant 20. The permanent side edge seams 51 may be formed as disclosed in U.S. Pat. Nos. 5,779,831, 5,772,825, 5,607,537, 5,622,589, 5,662,638, 6,042,673, and 6,726,792, for example. The aforementioned patents also disclose various processing methods to produce pants.

Refastenable Member

In one embodiment, referring to FIGS. 1-8, the pant 20 of the present disclosure may comprise the side edge seam 51 (e.g., permanent bonds) that may form the initial waist opening circumference 60 and leg openings 62, a first fastening component 53 disposed at or adjacent to the side edge seam 51, a second fastening component 55 disposed in the area defined between the first fastening component 53 and the longitudinal axis 42. The first and second fastening components 53 and 55 may be disposed on the same surface of the pant 20 (i.e., exterior surface 104 or interior surface 102) and/or in the same waist region (i.e., front waist region 36 or back waist region 38) of the pant 20. In one embodiment, a separation zone 59a may be disposed in the same waist region as the first fastening component 53a and/or in the same waist region as the second fastening component 55. In one embodiment, the second fastening component 55 may not be a specific distinct element and may be formed by a portion of one of the layers forming the pant 20, e.g., a portion of the backsheet 83. In such an embodiment, the second fastening component 55 may be disposed on or form a portion of the same surface to which the first fastening component 53 is disposed. In one embodiment, the first and second fastening components 53 and 55 are not in contact and/or are not attached or engaged with each other when packaged (i.e., prior to use).

In one embodiment, the first and/or the second fastening components 53 and 55, respectively, may each comprise at least one of a fastening surface and an attachment surface. The fastening surface may comprise a fastener, a fastening device, and/or a fastening composition, for example. The fastening surface may be used to attach the fastening component to a fastening surface of another fastening component or to another portion of the absorbent article 10 or the pant 20. The attachment surface may be used to attach the first and/or second fastening components 53 and 55 to the chassis 100, a portion of the front waist region 36, or another portion of the absorbent article 10, for example. In one embodiment, the second fastening component 55 may not comprise an attachment surface as it may be integrally formed with or may be a portion of the front waist region 36. In such an embodiment, the second fastening component 55 may still comprise a fastening surface, such that it can be attached to the first fastening component 53.

In one embodiment, the first and second fastening components 53 and 55 may be disposed on the exterior surface 104 of the absorbent article 10 in the front waist region 36. In an alternative embodiment where the absorbent article 10 comprises side panels 189, the first and second fastening components 53 and 55 may be disposed on or form a portion of one of the interior or exterior surfaces of the side panels 189 in the front waist region 36, for example.

In various embodiments, each of the fastening components 53 and 55 may be permanently bonded, formed with, or adhered or otherwise joined directly or indirectly to the pant 20 in the front waist region 36. One or more of the fastening components 53 and 55 may be permanently bonded or joined at a location at or proximate to the side edges 137 of the pant 20 by any suitable methods, such as adhesive bonding, sonic bonding, pressure bonding, thermal bonding or combinations thereof, for example.

In one embodiment, the first fastening component 53 and/or the second fastening component 55 may be made of a suitable releasably engageable fastener. For example, the first and second fastening components 53 and 55 may comprise mechanical fasteners, e.g., hook and loop fasteners, hook and hook fasteners, mechanical fasteners, macro-fasteners, buttons, snaps, tab and slot fasteners, tape fasteners, adhesive fasteners, cohesive fasteners, magnetic fasteners, hermaphrodidic fasteners, and other suitable fasteners. Some suitable examples of fastening systems and/or the fastening components 53 and 55 are discussed in U.S. Pat. Nos. 3,848,594, 4,662,875, 4,846,815, 4,894,060, 4,946,527, 5,151,092, 5,221,274, 6,251,097, 6,669,618, 6,432,098, 7,101,359, and 7,407,468.

Non-Engagement Zone

In one embodiment, referring to FIGS. 1 and 2, for example, the absorbent article 10 may comprise one or more non-engagement zones 54 disposed on or forming a portion of the same surface and in the same waist region as the first fastening components 53. In various embodiments, the non-engagement zones 54 may be intended to prevent, or at least inhibit, the first fastening components 53 from becoming engaged with other elements of the absorbent article 10 when packaged. In certain embodiments, the non-engagement zones 54 may be in surface to surface contact with a fastening surface of the first fastening components 53 when the pant 20 is packaged. In one embodiment, the non-engagement zone 54 may be disposed laterally inward of the first fastening component 53 as shown in FIGS. 1 and 2. The non-engagement zone 54 may be disposed at or adjacent the permanent side edge seam 51. In various embodiments, the non-engagement zones 54 may comprise a film, a sheet, a coating, or another material that does not attach to or engage with the first fastening components 53. Suitable non-engagement zone materials may comprise films of polyethylene or poly propylene, Teflon, latex, non-tack adhesives, selective adhesives, cohesives, and other materials that do not engage with the first fastening component 53.

Separation Zone

In order to minimize the level of tensile force required to tear open or separate the pant 20 at a predetermined location for removal from the wearer, a separation zone 59 may be provided at or proximate to the side edge seams 51. The separation zone 59 may be located in the intact, initial waist opening circumference 60 of the pant 20 in the same waist region as the first fastening component 53 and the second fastening component 55, as shown in FIGS. 1-3 and 5-8, for example. In an embodiment, a portion of the separation zone 59 may be disposed laterally inward of the first fastening component 53. For embodiments comprising the first and second fastening components 53 and 55, a portion of the separation zone 59 may be disposed between the first and second fastening components 53 and 55 and may be disposed in the same waist region as the first and second fastening components 53 and 55.

In one embodiment, the separation zone 59 may be located on the pant 20 in any manner that provides the desired functionality and ease of application and refastening. For example, a separation zone 59 may be located laterally inward of the side edges 137 of the absorbent article 10 in one or both of the front waist region 36 and back waist region 38. In various embodiments, the separation zone 59 may be disposed adjacent to or be included in the area encompassed by the fastening components 53 and 55, for example. In various embodiments, the separation zone 59 may be disposed between the first fastening component 53 and the second fastening component 55. In other embodiments, a portion of the separation zone 59 may be disposed laterally inward of the first side edge seam 5 1 and the first fastening component 53 may be disposed between the side edge seam 51 and the first longitudinally extending side edge 137*a*, for example. In one embodiment, a portion of the separation zone 59 may be disposed laterally inward of the first fastening component 53 or the first fastening component 53 may be disposed laterally inward of the separation zone 59. In other embodiments, the first fastening component 53 may be disposed laterally between the first longitudinally extending side edge 137*a* and the first side edge seam 51*a*.

While the separation zone 59 is illustrated as a dotted line in certain embodiments for simplicity, it will be understood that the separation zone 59 may, in fact, be a "zone" having an area verses a line. The separation zone 59 may be any suitable size for a particular pant. In one embodiment, a caregiver may have an option of separating the separation zone 59 at more than one place within the separation zone 59, for example.

In one embodiment, the separation zone 59 may be formed in a layer or a laminate of layers by any methods that encourage preferentially fracture or separation when stress is applied thereto. The separation zone 59 may also be formed by a variety of methods and may comprise a variety of patterns. In one embodiment, the separation zone 59 may comprise a pattern providing greater strength in the cross-machine or lateral direction (CD) than the strength in the machine or longitudinal direction (MD), for example. This configuration may help to maintain a pant-like form during application and use, and yet provide the ease of opening to enable removal of the pant 20 or enable application as a traditional tape-style diaper rather than a pant. In other embodiments, the separation zone 59 may not comprise a weakened area, but instead, the area of the pant 10 surrounding the separation zone 59 may comprise a strengthened area, for example. In such an embodiment, the transition between the strengthened area and the adjacent area may form an area of stress concentration which can be utilized to help propogate the separation of the separation zone 59.

In one embodiment, each of the laterally opposing separation zones 59 may comprise laterally opposing separation zone edges that may be formed in one of the waist regions 36 and 38 laterally inward of the first fastening components 53. In such an embodiment, the separation zone edges may intersect with the front waist end edge 136 laterally inboard the side edge 137 and may intersect the side edge 137 of the absorbent article 10 at the margin of each leg opening 62. In other embodiments, the separation zone edges may also be disposed in other locations on the absorbent article 10. For example, if the separation zone edges continued generally linearly toward the lateral axis 44, continuous portions of the pant 20 may remain in place around the legs of the wearer. When the separation zone edges are shaped to intersect the margins of the respective leg opening 62 as described above, tearing or separating the pant 20 at both of the laterally opposing separation zone edges may release the pant 20 from the waist and both legs of the wearer. In one embodiment, the separation zone 59 may comprises a first separation zone edge extending from the waist opening of the absorbent article 10 to one of the leg openings of the absorbent article 10, and a second separation zone edge extending from the waist opening of the absorbent article 10 to the laterally opposing leg opening of the absorbent article 10. In various embodiments, the first and second separation zone edges may be linear, non-linear, parallel, or non-parallel.

In one embodiment, the separation zone 59 may comprises a bond, such as a sonic sealed bond, a thermal sealed bond, a high pressure bond, a radio frequency bond, an adhesive bond, a cohesive bond, a sewed bond, an autogenous bond, and a combination thereof, for example. In such embodiments, the bond area may form an area of increased strength forming an area of stress concentration immediately adjacent. This area of stress concentration may help enable separation of the separation zone. In an alternative embodiment, the bond can be separated (not illustrated) to create the separation zone.

In one embodiment, the initial waist opening circumference 60 is configured to be opened by separating a first portion of the separation zone 59 from a second portion of the separation zone 59. The separation of the first portion of the separation zone 59 from the second portion of the separation zone 59 may create linear or non-linear separation edges through, or at least partially through, the separation zone 59.

In certain embodiments, a separation zone locator or visual signal comprising one or more structural, graphical or textural elements may be provided so a caregiver can clearly distinguish the separation zone 59 from the remainder of the pant 20. For example, a separation zone locator may be printed at or adjacent to the separation zone 59. In such an embodiment, the presence of the visible separation zone locator may prove helpful to the caregiver in locating the separation zone 59 for use in removal of the pant 20.

In one embodiment, referring to FIG. 8, a finger tab 72 may be disposed at or adjacent the side edge seam 51 allowing the caregiver to use the finger tab 72 to release the first fastening component 53 from the exterior surface 104 of the pant 20 (in one embodiment, by breaking the closure bond) and, subsequently, to break the separation zone 59. The finger tab 72 may be disposed adjacent the first fastening component 53 and extend beyond the side edge 137 of the pant 20. In other embodiments, the finger tab 72 may form a portion of the surface on which the first fastening component 53 is disposed.

Accordingly, the finger tab 72 may be partially aligned with the separation zone 59 as shown in FIG. 8. It should be appreciated, however, that the tab 72 may alternatively be positioned and arranged in any alternative manner that facilitates intentional opening of the separation zone 59. For instance, the tab 72 may extend substantially along the entire length of the separation zone 59. The tab 72 may be configured to be grasped by a caregiver when applying an opening or releasing force to the first fastening component 53 and the separation zone 59 in order to sever the initial waist opening circumference 60 and leg opening circumferences 62 to remove the pant 20 from the wearer. The tab 72 may also provide a visual grasping point and greater leverage for the caregiver to open the first fastening components 53 and sever the separation zone 59 and, in some embodiments, the closure bond.

In one embodiment, the tab 72 may comprise any suitable indicia that can be printed on the exposed surface of the tab 72 (i.e., the surface that is visible when the pant 20 is being worn). Alternatively, the indicia may be disposed on an auxiliary layer that is affixed to the tab 72, for example. Accordingly, the indicia may be visible to a caregiver who wishes to remove the pant 20 from the wearer.

In one embodiment, suitable indicia may comprise graphics, writings, (e.g., "pull here" or "open here" or other suitable language that communicates the use of the tab 72), regions that are colored differently than surrounding pant 20 components, such as the chassis 100, and combinations thereof that increase the visibility and intuitive use of the tab 72. Furthermore, the finger tab 72, the first fastening component 53, the non-engagement zone 54, the second fastening component 55, and the separation zone 59 may comprise distinctively different colors, patterns, characters, or carry other identifying indicia that provides contrast between the various components, thereby increasing their visibility and communicating their intuitive use to the caregiver. In various embodiments, the indicia may comprise pictorial symbols, photographs, drawings, cartoons, and logos, for example. The indicia 76 may also comprise a single icon or a series of the same or different icons. Graphics other than the images described above may be used to attract a caregiver's attention and indicate a gripping location, as described in U.S. Pat. Publ. Nos. 2006/0212010 and 2006/0212018, for example.

As described above, the separation zone 59 may be configured to be broken, separated, or severed, such that the caregiver may easily separate a portion of the front waist region 36 from itself or may separate a portion of the back waist region 38 from itself to inspect the pant 20 for soiling or to initially apply the pant 20 in a traditional tape-style diaper fashion, if desired, and also to remove the pant 20 from the wearer after it has been soiled. In one embodiment, the separation zone 59 may have an opening force of less than about 5000 grams, less than about 4000 grams, or less than about 3000 grams such that the caregiver can choose to break the separation zone 59 and remove the pant 20. Alternatively, the separation zone 59 may be left intact allowing a caregiver or a wearer to slide down the pant 20 from the waist and legs similar to conventional underwear, for example. In one embodiment, the separation zone 59 may comprise a notch or a notched portion (not illustrated). In one embodiment, the notch may help get the separation or tearing of the two separation zone edges in an area of the separation zone 59, for example. In various embodiments, indicia or graphics may be oriented on a portion of the separation zone 59 (e.g., in the middle of the separation zone) such that the caregiver tears or separates the separation zone in that desired location. In such an embodiment, the separation may not be assisted by weakened areas, perforations, one material being positioned adjacent another material, etc. In one embodiment, the resulting separation may be very rough, jagged, and/or unpredictable, for example.

Example Embodiments

In one embodiment, referring to FIGS. 1-7, when the pant 20 is worn on the lower torso of a wearer, the front waist end edge 136 and the back waist end edge 138 of the chassis 100 may encircle a portion of the waist of the wearer, while at the same time the side edges 137a and 137b may encircle at least a portion of the legs of the wearer. At the same time, the crotch region 37 may be generally positioned between the legs of the wearer and the absorbent core 200 may extend from the front waist region 36 through the crotch region 37 to the back waist region 38.

Flange Seam Progression Figures

In one embodiment, referring to FIGS. 9-14 the absorbent article 10 may be folded about a lateral axis 44 to form a pant 20 comprising flange seams 58. The absorbent article 10 may comprise a front waist region 36 comprising a front waist end edge 136, a back waist region 38 comprising a back waist end edge 138, one or more first fastening components 53, one or more non-engagement zones 54, optionally, one or more closure bonds 56, and a longitudinal axis 42. In one embodiment, the one or more closure bonds 56 may not be present until the absorbent article 10 is folded about the lateral axis 44 and readied to be formed into the pant 20. In various embodiments, the absorbent article 10 may comprise one or more first fastening components 53 disposed in a first waist region and may optionally comprise one or more second fastening components 55 disposed in the same waist region as the first fastening components 53. The one or more second fastening components 55 may be formed as a portion of the first waist region, formed integral with a portion of the first waist region, or attached to or disposed on a portion of the first waist region. In one embodiment, more than two second fastening components 55 may be provided along an area of the first waist region, for example. In various embodiments, the first fastening components 53 and the second fastening components 55 may be disposed in the same waist region (e.g., the first waist region 36) and on the same surface of the same waist region (e.g., the exterior surface 104).

Now described is the progression of how the absorbent article 10 may be formed into the pant 20 (i.e., steps taken by the manufacturer). In one embodiment, referring to FIG. 9, a simplified version of the absorbent article 10 is illustrated. While the absorbent article 10 is illustrated as being comprised of a single panel, those of skill in the art will recognize that the absorbent article 10 may be comprised of multiple panels or components, such as topsheets, backsheets, containment regions, absorbent cores, leg cuffs, waistbands, elastics and/or side panels, for example. The simplified version is illustrated merely for simplicity in the explanation of the progression of formation. To form the pant 20, first, the absorbent article 10 is folded about the lateral axis 44 such that the interior surface 102 of the front waist region 36 is brought into a surface-to-surface facing position relative to the interior surface 102 of the back waist region 38. In one embodiment, this configuration is illustrated in FIG. 10. While in the configuration of FIG. 10, laterally opposing flange seams 58a and 58b are formed near the side edges 137a and 137b, respectively. At this stage, the front waist region 36 is joined to the back waist region 38 via the flange seams 58 and a separation zone 59 may be formed intermediate each first fastening component 53 and each non-engagement zone 54 on the front waist region 36. As can be seen in FIG. 10, the pant 20 comprises an initial waist opening circumference 60 formed by the permanent side edge seams 51. Optionally, in the step illustrated in FIG. 10, one or more closure bonds 56, may be formed by various methods, such as adhesive bonding, cohesive bonding, thermal bonding, ultrasonic bonding, or pressure bonding, for example. The closure bonds 56 may be disposed on the exterior surface 104 of the front waist region 36 at or adjacent each side edge 137 and/or each first fastening component 53. Next, referring to FIG. 11, the portions of the absorbent article 10 that comprise the flange seams 58 and/or the first fastening components 53 can be folded laterally inward, in a direction toward the longitudinal axis 42. In one embodiment, the closure bonds 56 may hold the folded over portion against the exterior surface 104 of the front waist region 36 of the pant 20. In various embodiments, the fully formed pant 20 is illustrated in FIG. 11. As can be seen in FIG. 11, the fully formed pant 20 comprises an initial waist opening circumference 60. In such an embodiment, the first fastening components 53 are not used to maintain or form the initial waist opening circumference 60 and, in fact, are not fastenably engaged with the second fastening components 55 or other portions of the pant 20 although they may be in contact with the non-engagement zones 54. As discussed herein, the non-engagement zones 54 prevent, or at least inhibit, the first fastening components 53 from fastening with a portion of the pant 20 when packaged. In certain instances, the consumer (e.g., caregiver) would receive the pant 20 in the configuration illustrated in FIG. 11.

In one embodiment, the caregiver, upon receipt of the pant 20 or removal of the pant 20 from a package (the pant 20, in one embodiment, being in the configuration illustrated in FIG. 11), may decide to apply the pant 20 as a pull-on training pant or as a type-style diaper. To apply the pant 20 as a pull-on training pant, the caregiver may use the pant 20 like underwear and have the wearer place one foot in each leg openings and pull the pant 20 up to an area about the wearer's waist. In this configuration, the first fastening components 53 would not be fastenably engaged with a portion of the pant 20 or with the second fastening components 55. Instead, the flange seam 58 would maintain the initial waist opening circumference 60 around the wearer's waist. If the caregiver needs to check the pant 20 at any time during use by the wearer, the caregiver can pull on a portion of the pant adjacent the side edge 137 to separate or break the closure bond 56 and then rotate the folded over portion away from the longitudinal axis 42 thereby separating or tearing the separation zone 59. In one embodiment, the separated or torn separation zones 59 are illustrated in FIG. 12. In various embodiments, one or more portions of the front waist region 36 that have been separated from the central portion of the front waist region 36 may then be reattached to the front waist region 36, similar to the example configuration illustrated in FIG. 14. When the pant 20 is in the configurations of FIGS. 12 and 13, the caregiver can check the pant 20 to determine if a pant change needs to be made. If a pant change does not need to be made, the caregiver can refasten the pant 20 by engaging the first fastening components 53 and the second fastening components 55 with each other to create a second waist opening circumference 61. One embodiment of such engagement is illustrated in FIG. 14. In embodiments, where the second fastening components 55 are not provided, the caregiver may engage the first fastening components 53 with another portion of the front waist region 36 (e.g., the backsheet 83).

In one embodiment, to apply the pant 20 as a type-style diaper, the caregiver can pull on a portion of the pant adjacent the side edge 137 to separate or break the closure bond 56 and rotate the folded over portion away from the longitudinal axis 42 thereby separating or tearing the separation zone 59. In one embodiment, this configuration is illustrated in FIG. 12. Referring to FIG. 13, the pant 20 may then be unfolded about the lateral axis 44. When the pant 20 is unfolded, in one embodiment, referring to FIG. 13, one or more portions of the front waist region 36 may remain attached to the back waist region 38. In this configuration the pant 20 can be applied to the wearer like a tape-style diaper. In one embodiment, the applied configuration is illustrated in FIG. 14. In FIG. 14, the first fastening components 53 are engaged with the second fastening components 55 or other portions of the front waist region 36 to create a second waist opening circumference 61.

Example Embodiments

In one embodiment, referring to FIGS. 15-17, the laterally opposing permanent side edge seams 51 (flange seams 58) may be disposed at or adjacent the side edge 137 in one or both of the waist regions 36 and 38. In embodiments where the lateral extent of the front waist region 36 is substantially equal to the lateral extent of the back waist region 38 during bonding of the permanent side edge seams 51, the permanent side edge seams 51 may be disposed at or adjacent the side edges 137 of the pant 20 in both the front and back waist regions 36 and 38 as shown in FIG. 15. In one embodiment, the absorbent article 10 may be folded at a laterally extending fold line disposed in the crotch region to bring the front waist region 36 and the back waist region 38 into an interior surface-to-interior surface, face-to-face orientation. Subsequently, the permanent side edge seams 51 may be formed by bonding the interior surface of one waist regions 36 or 38 to the interior surface of the opposing waist region 36 or 38. The first fastening component 53 and the optional second fastening component 55 may be applied to the absorbent article 10 before formation of the permanent side edge seams 51 or after formation of the permanent side edge seams 51. In such an embodiment, after the permanent side edge seams 51 are formed, a portion of the pant 20 comprising the first fastening component 53 and/or the permanent side edge seam 51 may be folded laterally inward thereby positioning the fastening surface of the first fastening component 53 in a face-to-face, surface-to-surface orientation with a non-engagement zone 54. The laterally inward folded portion of the pant 20 chassis 100 comprising the first fastening component 53 and/or the permanent side edge seam 51 may be releasably attached to the surface of the absorbent article 10, using a closure bond 56, for example, to maintain the position of the first fastening component 53 until the closure bond 56 is broken by the caregiver. When removed from a package, the absorbent article 10 is already formed into the pant 20. The caregiver may apply the pant 20 to the wearer in pant form or as a tape-style diaper by first releasing the fastening component 53 by unfolding the laterally inwardly folded portion of the pant 20 (by breaking the closure bond 56, for example), breaking the initial waist opening circumference by separating the separation zone 59, separating a portion of the front waist region 36 from itself, placing the back waist region 38 of the absorbent article 10 under the wearer and fastening the first fastening component 53 disposed on a portion of the front waist region 36 to the second fastening component 55 disposed on or forming a potion of the front waist region 36, thereby forming the second waist opening circumference and re-closing the pant 20.

When referring to various flat and cross-sectional example embodiments below, like numbering denotes like features, although not all similar features are labeled in each view. In one embodiment, FIG. 16 is a simplified flat, uncontracted illustration of the pant 20 of FIG. 15. In one embodiment, referring to FIG. 16, the second fastening component 55 can extend a substantial portion of the distance between the non-engagement zone 54a and the non-engagement zone 54b. In other embodiments, the second fastening component 55 may not be a separate component but, instead, may form a portion of one of the components of the pant 20, such as the backsheet 83, for example. In other embodiments, the second fastening component 55 may comprise one or more elements. In one embodiment, FIG. 17 is a cross-sectional view of FIG. 16 taken along line A-A. FIGS. 1 and 2 denote other embodiments of the absorbent article 10 that may be formed into the pant 20, as described in greater detail above. In FIGS. 1 and 2, the second fastening component is shown as forming a portion of the exterior surface of the absorbent article 10 in the front waist region and the first fastening component 53 may be attached to a portion of the front waist region 36. In another embodiment, FIG. 18 is a simplified flat, uncontracted illustration of an absorbent article 10 that may be formed into a pant. FIG. 18 illustrates an embodiment, where two separate second fastening components 55a and 55b are present. In one embodiment, first fastening component 53a may be engaged with second fastening component 55a and first fastening component 53b may be engaged with second fastening component 55b to form a second waist opening circumference 61 in the pant 20. In such an embodiment, at least one of the first fastening components 53 may also be engaged with other portions of the front waist region 36, for example. FIG. 19 is a cross-sectional view of FIG. 18, taken along line A-A, illustrating, among other things, the second fastening components 55a and 55b. FIG. 20 is a cross-sectional view of FIG. 1, taken along line B-B. In one embodiment, FIG. 20 illustrates a first fastening component 53a, a separation zone 59a and a non-engagement zone 54a.

In one embodiment, referring to FIGS. 21 and 22, one of the front and back waist regions 36 and 38 may be folded prior to the creation of the permanent side edge seams 51 such that the lateral extent of front waist region 36 is substantially equal to the lateral extent of the back waist region 38 during bonding of the permanent side edge seams 51. In such an embodiment, the resulting permanent side edge seams 51 may be disposed at or adjacent the side edges 137 of the absorbent article 10 in one of the waist regions 36 or 38 and disposed laterally outward of the side edge 137 of the absorbent article 10 in the opposing waist region 36 or 38. In one embodiment, the absorbent article 10 may be folded at a laterally extending fold line disposed in the crotch region 37 to bring the front waist region 36 and the back waist region 38 into an interior surface-to-interior surface, face-to-face orientation. The first fastening component 53 and the optional second fastening component 55 may be applied to the absorbent article 10 prior to forming the permanent side edge seam 51. In such an embodiment, prior to forming the permanent side edge seam 51 the portion of the absorbent article 10 comprising the first fastening component 53 may be folded laterally inward thereby positioning the fastening surface of the first fastening component 53 in a face-to-face, surface-to-surface orientation with the non-engagement zone 54. The laterally inward folded portion of the pant 20 comprising the first fastening component 53 may be releasably attached to the exterior surface 104 of the absorbent article 10 (using closure bond 56, for example) to maintain the position of the first fastening component 53 until it is released by the caregiver. Subsequently, the permanent side edge seams 51 may be formed by bonding the interior surface of one waist regions 36 or 38 to the interior surface of the opposing waist region 36 or 38. When removed from the package, the absorbent article 10 is in the form of the pant 20. The caregiver may apply the pant 20 to a wearer as a pull-on training pant or as a tape-style diaper by unfolding the laterally inwardly folded portion of the absorbent article comprising the first fastening component 53, breaking the initial waist opening circumference 60, placing the back waist region 36 of the absorbent article 10 under the wearer and fastening the first fastening component 53 to the second fastening component 55 or another portion of the absorbent article 10 thereby forming the second waist opening circumference 61 and re-closing the pant 20. In one embodiment, FIG. 22 is illustrated with both separation zones 59 separated and a first side in the unattached configuration and a second side in the reattached configuration.

In an embodiment of the pant 20 where the lateral extent of the absorbent article 10 in one of the waist regions 36 or 38 is greater than the lateral extent of the absorbent article 10 in the opposing waist region 36 or 38, i.e. forming one wider waist region and one narrower waist region, referring to FIGS. 23 and 24, during bonding the permanent side edge seams 51, the permanent side edge seams 51 may be disposed at or adjacent the side edge 137 of the narrower of the waist regions 36 or 38 and be disposed laterally inward of the side edge 137 of the wider waist region 36 or 38, i.e. the waist region having greater lateral extent, In one embodiment, the absorbent article 10 may be folded about a laterally extending fold line disposed in the crotch region 37 to bring the front waist region 36 and the back waist region 38 into an interior surface-to-interior surface, face-to-face orientation. Subsequently, the permanent side edge seams 51 may be formed by bonding the interior surface of one waist regions to the interior surface of the opposing waist region. The first fastening component 53 or the optional second fastening component 55 may be applied to the absorbent article 10 before or after forming the permanent side edge seams 51. In such an embodiment, after the permanent side edge seams 51 are formed, a portion of the absorbent article 10 comprising the first fastening component 53 and/or the permanent side edge seam 51 may be folded laterally inward thereby positioning the fastening surface of the first fastening component 53 in a face-to-face, surface-to-surface orientation with a non-engagement zone 54. The laterally inward folded portion of the pant 20 comprising the first fastening component 53 and/or the permanent side edge seam 51 may be releasably attached to the surface of the absorbent article 10 to maintain the position of the first fastening component 53 until it is released by the caregiver (e.g., by breaking the closure bond 56). When removed from the package, the absorbent article 10 is in the form of the pant 20. The caregiver may apply the absorbent article 10 to the wearer as a pull-on training pant or as a tape-style diaper by unfolding the laterally inwardly folded portion of the pant 20, breaking the initial waist opening circumference 60, placing the back waist region 38 of the absorbent article 10 under the wearer and fastening the first fastening component 53 to the second fastening component 55 or other portion of the absorbent article 10 thereby reclosing the pant 20 to form the second waist opening circumference 61. In one embodiment, FIG. 24 is illustrated with both separation zones 59 separated and a first side in the unattached configuration and a second side in the reattached configuration.

In one embodiment, referring to FIGS. 25 and 26, another pant 20 is illustrated. In one embodiment, FIG. 26 is illustrated with both separation zones 59 separated and a first side in the unattached configuration and a second side in the reattached configuration. In one embodiment, FIG. 27 illustrates a simplified flat that can be used to create the embodiments illustrated in FIGS. 23, 24, 25, and 26. In one embodiment, FIG. 28 illustrates a cross-sectional view of FIG. 27, taken along line A-A. In one embodiment, FIG. 29 illustrates an alternative (to FIG. 28) cross-sectional view of FIG. 27, taken along line B-B. FIGS. 30A-H illustrate alternative embodiments of side panels, labeled 189c-189j and first fastening components, labeled 53c-53j.

In one embodiment, referring to FIGS. 31-34, the lateral extent of the absorbent article 10 in one of the waist regions 36 and 38 is greater than the lateral extent of the absorbent article 10 in the opposing waist region, i.e. forming a narrower waist region, prior to or during bonding of the permanent side edge seams 51, the waist region 36 or 38 having the greater lateral extent is folded and overlapped with the narrower waist region 36 or 38 thereby forming the permanent side edge seam 51 that may be disposed at or adjacent the side edges 137 of both the front and rear waist regions 36 and 38 of the absorbent article 10. In the embodiment, the absorbent article 10 is folded at a laterally extending fold line disposed in the crotch region to bring the front waist region 36 and the back waist region 38 into an interior surface-to-interior surface, face-to-face orientation. The first fastening component 53 may be applied to the absorbent article 10 prior to forming the permanent side edge seam 51. The optional second fastening component 55 may also be applied prior to forming the permanent side edge seam 51 or after forming the permanent side edge seam 51. In this embodiment, prior to forming the permanent side edge seam 51, the portion of the absorbent article 10 comprising the first fastening component 53 is folded laterally inward thereby positioning the fastening surface of the first fastening component 53 in a face to face surface to surface orientation with the non-engagement zone 54. The laterally inward folded portion of the absorbent article 10 comprising the first fastening component 53 is releasably attached to the exterior surface 104 of the absorbent article 10 to maintain the position of the first fastening component 53 until it is released by the caregiver (e.g., by breaking the closure bond 56). Subsequently, the permanent side edge seams 51 may be formed by bonding the interior surface of one waist regions 36 or 38 to the interior surface of the opposing waist region 36 or 38. When removed from the package, the absorbent article 10 is in the form of the pant 20. The caregiver may apply the absorbent article 10 to the wearer as a pant or as a tape-style diaper by unfolding the laterally inwardly folded portion of the pant 20 (by breaking the closure bond 56, for example), breaking the initial waist opening circumference 60, placing the back waist region 38 of the absorbent article 10 under the wearer and fastening the first fastening component 53 to the second fastening component 55 or to another portion of the front waist region 36 thereby re-closing the pant and forming a second waist opening circumference 61. In one embodiment, FIG. 32 is a simplified flat absorbent article 10 that can be used to form the pant 20 of FIG. 31. FIG. 33 is a cross-sectional view of the absorbent article 10 of FIG. 32 taken along line A-A. FIG. 34 is a cross-sectional view of the absorbent article 10 of FIG. 32 taken along line B-B.

Attorney Docket No. 11577P, filed on Jan. 20, 2010, naming Gary Dean LaVon as an inventor, generally discloses various acceptable product features that may be implemented in the embodiments described in the present application. Specifically, the above-described embodiments may, as appropriate, comprise a fastening system and side panels as described in Attorney Docket No. 11577P.

Method of Making

The following method of making description refers generally to FIG. 35. Like element references from above will apply below even if they are not illustrated in FIG. 35.

In one embodiment, provided is a bifold assembly system for folding an absorbent article 10 along a laterally extending axis 44. The system may comprise a first vacuum conveyance 630, for example a vacuum drum that has an outer surface for receiving discrete absorbent articles 10. The first vacuum conveyance 630 may transport the discrete absorbent article 10 in the machine direction. The absorbent article 10 having a leading half comprising the front waist region 36 and the front half of the crotch region 37, i.e. the portion of the crotch region 37 disposed between the lateral axis 44 and the front waist region 36, and a trailing half comprising the back waist region 38 and the back half of the crotch region 37, i.e. the portion of the crotch region 37 disposed between the lateral axis 44 and the back waist region 38. The system may comprise a second vacuum conveyance 645, for example a second vacuum drum, disposed adjacent to the first vacuum conveyance 630. The second vacuum conveyance 645 may be configured to receive at least a portion of the leading half of the absorbent article 10 from the first vacuum conveyance 630. The second vacuum conveyance 645 may be configured to apply a peel force such that at least part of the leading half of the absorbent article 10 is transferred from the first vacuum conveyance 630 to the second vacuum conveyance 645 and held on the surface of the second vacuum conveyance 645. The system may comprise a third vacuum conveyance, for example a vacuum conveyor, disposed proximate the first and second vacuum conveyances 630 and 645. The third vacuum conveyance may comprise a drive mechanism for moving the surface of the third vacuum conveyance at a first speed, a second speed, in a first direction and in a second direction.

In one embodiment of the method of making, a continuous web comprising a plurality of interconnected backsheets 83 is combined with a series of laterally opposing pairs of discrete side panels 189. The side panels 189 may comprise a material that is elastically extensible and may additionally comprise a refastenable fastening component disposed on a surface of the side panel 189. The continuous web of interconnected backsheets 83 is subsequently joined with a continuous web comprising a plurality of interconnected topsheets 81. Discrete absorbent cores 200 are disposed between the continuous backsheet 83 web and the continuous topsheet 81 web thereby forming a plurality of interconnected absorbent containment assemblies. The web is severed to form a plurality of discrete absorbent articles 10. A discrete absorbent article 10 is placed on the outer surface of a first vacuum conveyance 630. Alternatively, the continuous web of interconnected absorbent articles 10 may be placed on the first vacuum conveyance 630 prior to severing the web into discrete absorbent articles 10. The first vacuum conveyance 630 may be in the form of a vacuum drum as shown in FIG. 35 or alternatively in the form of a movable foraminous vacuum conveyor belt configured in an endless loop. The absorbent article 10 is transported along the surface of the first vacuum conveyance 630 in a direction toward a second vacuum conveyance 645. The second vacuum conveyance 645 may be in the form of a vacuum drum as shown in FIG. 35 or alternatively in the form of a movable foraminous vacuum conveyor belt configured in an endless loop. A portion of the leading half of the absorbent article 10 comprising the front waist region 36 and the front half of the crotch region 37 is transferred from the first vacuum conveyance 630 to the second vacuum conveyance 645. Bifold clamps (not shown) hold the crotch region 37 at or adjacent the lateral axis 44 in contact with the first vacuum conveyance 630 thereby helping to maintain the trailing half of the absorbent article 10 comprising the back half of the crotch region 37 and the back waist region 38 in contact with the surface of the first vacuum conveyance 630. The surfaces of the first vacuum conveyance 630 and second vacuum conveyance 645 downstream of the transfer point are moving in directions that are divergent from one another. The leading half of the absorbent article 10 is transported along the surface of the second vacuum conveyance 645 until it is transferred to a third vacuum conveyance 670. The surfaces of the third vacuum conveyance and the second vacuum conveyance 645 are convergent. The bifold clamp not only helps retain the crotch region 37 in contact with the first vacuum conveyance 630 but it also helps retain tension in the absorbent article 10 as it is bifolded. The leading half of the absorbent article 10 travels along the surface of the third vacuum conveyance as the trailing half of the absorbent article 10 travels along the surface of the first vacuum conveyance 630 thereby forming a bifolded absorbent article 10. At this point the surface of the third vacuum conveyance and the surface of the first vacuum conveyance 630 are moving in a convergent direction. U.S. Pat. Publ. No. 2009/0098995A1, entitled System for Bifolding an Absorbent Article, generally discloses various acceptable embodiments for carrying out the process as described above and as described in the present application's FIG. 35. More specifically, the first vacuum conveyance (folding drum), second vacuum conveyance (peel roll), third vacuum conveyance (bifold conveyor) as disclosed in U.S. Pat. Publ. No. 2009/0098995A1 may be used in the process of the present application.

In one embodiment, the trailing half of the absorbent article 10 comprising the back waist region 38 may comprise side panels 189 having refastenable fastening components disposed thereon. The side panels 189 are held in place by vacuum created by the first vacuum conveyance 630. Once the absorbent article 10 has been bifolded, a portion of the side panel 189, such as the portion comprising the refastenable fastening components may be folded laterally inward to engage the fastening components disposed in the back waist region 38 with the front waist region 36 of the absorbent article 10. The side panels 189 may be folded laterally inward by means of a fourth vacuum conveyance such as a vacuum twist belt or alternatively the side panels 189 may be folded laterally inward by a folding board or other suitable methods. In an alternative embodiment, the side panels 189 may be folded by a folding mechanism disposed on a portion of the first vacuum conveyance 630.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description are, in relevant part, incorporated herein by reference in their entirety. The citation of any document is not to be construed as an admission that it is prior art with respect to the present disclosure. To the extent that any meaning or definition of a term in the present disclosure conflicts with any meaning or definition of the term in a document incorporated by reference, the meaning or definition assigned to the term in the present disclosure document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. An absorbent article comprising:
a back waist region comprising first and second side panels, a front waist region, a crotch region disposed between the front waist region and the back waist region, a front waist end edge, a back waist end edge, a longitudinal axis extending from a mid-point of the front waist end edge to a mid-point of the back waist end edge, a first longitudinally extending side edge, a second longitudinally extending side edge, an exterior surface, an interior surface, a topsheet, a backsheet, and an absorbent core disposed between the backsheet and the topsheet;

wherein a portion of the front waist region and a portion of the back waist region are joined in a surface to surface relationship to form a pant comprising a first permanent side edge seam and a laterally opposed second permanent side edge seam, and wherein the first and second permanent side edge seams define an initial waist opening circumference and a pair of leg openings;

a first fastening component comprising a first fastening surface and a first attachment surface, wherein each of the first fastening surface and the first attachment surface are disposed on the first side panel, and wherein the first fastening surface comprises a first plurality of elements selected from the group consisting of hooks, bulbs, mushrooms, arrowheads, balls on stems, and combinations thereof, and wherein the first plurality of elements overlap, at least in part, the first permanent side edge seam, and wherein the first attachment surface is disposed on the exterior surface of the absorbent article, and wherein the first fastening surface is in contact with a first non-engagement surface and is capable of being refastenably engaged with the first attachment surface; and a second fastening component comprising a second fastening surface and a second attachment surface, wherein each of the second fastening surface and the second attachment surface are disposed on the second side panel, and wherein the second fastening surface comprises a second plurality of elements selected from the group consisting of hooks, bulbs, mushrooms, arrowheads, balls on stems, and combinations thereof, and wherein the second plurality of elements overlap, at least in part, the second permanent side edge seam, and wherein the second attachment surface is disposed on the exterior surface of the absorbent article, and wherein the second fastening surface is in contact with a second non-engagement surface and is capable of being refastenably engaged with the second attachment surface; and wherein the initial waist opening circumference formed by the first and second permanent side edge seams is configured to be opened.

2. The absorbent article of claim 1, comprising a separation zone disposed in the same waist region as one of the first fastening component and the second fastening component.

3. The absorbent article of claim 2, wherein the initial waist opening circumference is configured to be opened by separating a first portion of the separation zone from a second portion of the separation zone.

4. The absorbent article of claim 2, wherein the first fastening surface is free from refastenable engagement with the first attachment surface or another portion of the absorbent article prior to separation of a first portion of the separation zone from a second portion of the separation zone.

5. The absorbent article of claim 2, wherein a portion of the separation zone is disposed between the first fastening surface and the first attachment surface.

6. The absorbent article of claim 2, wherein a portion of the separation zone is disposed laterally inward of the first permanent side edge seam and the first fastening component is disposed between the first permanent side edge seam and the longitudinal axis.

7. The absorbent article of claim 2, wherein the separation zone, after separation, comprises:
  a first separation zone edge extending from the waist opening to one of the leg openings; and
  a second separation zone edge extending from the waist opening to one of the leg openings.

8. The absorbent article of claim 2, wherein the separation zone comprises a visual signal comprising one or more structural, graphical or textural elements.

9. The absorbent article of claim 2, wherein the separation zone comprises a bond, and wherein the bond is one of a sonic sealed bond, a thermal sealed bond, a high pressure bond, a radio frequency bond, an adhesive bond, a cohesive bond, a sewed bond, an autogenous bond, and a combination thereof.

10. The absorbent article of claim 2, wherein a portion of the separation zone is disposed laterally inward of the first fastening component.

11. The absorbent article of claim 2, wherein the first fastening component is disposed laterally inward of the separation zone.

12. The absorbent article of claim 1, wherein the first and second fastening surfaces consist of mushroom elements.

13. The absorbent article of claim 1, wherein the first fastening component is disposed laterally between the first longitudinally extending side edge and the first permanent side edge seam.

14. The absorbent article of claim 1, comprising a separation zone, wherein the absorbent article comprises only one first fastening component and only one second fastening component disposed in the same waist region as the separation zone.

15. The absorbent article of claim 1, wherein the first and second fastening surfaces consist of hook elements.

16. The absorbent article of claim 1, wherein the front waist region comprises third and fourth side panels, wherein the first and third side panels are joined to form the first permanent side edge seam and wherein the second and fourth side panels are joined to form the second permanent side edge seam.

17. The absorbent article of claim 16, wherein the first and second side panels are integral with the back waist region and wherein the third and fourth side panels are integral with the front waist region.

* * * * *